US012678330B2

(12) United States Patent
Smith et al.

(10) Patent No.: US 12,678,330 B2
(45) Date of Patent: Jul. 14, 2026

(54) TECHNIQUES FOR PERFORMING A SAFETY TEST OF A LASER DIODE OPHTHALMIC SURGICAL APPARATUS

(71) Applicant: Alcon Inc., Fribourg (CH)

(72) Inventors: Ronald T. Smith, Irvine, CA (US); Alireza Mirsepassi, Irvine, CA (US); Neda Dadashzadeh, Mission Viejo, CA (US); Yuchao Liu, Irvine, CA (US); Conrad Sawicz, Tustin, CA (US)

(73) Assignee: Alcon Inc., Fribourg (CH)

( * ) Notice: Subject to any disclaimer, the term of this patent is extended or adjusted under 35 U.S.C. 154(b) by 535 days.

(21) Appl. No.: 18/329,929

(22) Filed: Jun. 6, 2023

(65) Prior Publication Data

US 2023/0414413 A1 Dec. 28, 2023

Related U.S. Application Data

(60) Provisional application No. 63/366,784, filed on Jun. 22, 2022.

(51) Int. Cl.
*A61F 9/008* (2006.01)
*A61B 3/10* (2006.01)

(52) U.S. Cl.
CPC ........ *A61F 9/00823* (2013.01); *A61B 3/1015* (2013.01); *A61F 9/00825* (2013.01)

(58) Field of Classification Search
CPC .. A61F 9/008; A61F 9/00823; A61F 9/00825; A61B 3/1015; A61B 3/10; G01R 31/26; G01R 31/2635; G01R 31/2872; G01R 31/2874; G01R 31/3004; G01R 31/30; G01R 19/00; G01R 19/007; G01R 19/0092
See application file for complete search history.

(56) References Cited

U.S. PATENT DOCUMENTS

| | | | |
|---|---|---|---|
| 5,543,611 A | 8/1996 | Andrews | |
| 6,271,915 B1 | 8/2001 | Frey | |
| 6,629,638 B1 * | 10/2003 | Sanchez | G01R 31/002 |
| | | | 235/455 |
| 11,172,560 B2 | 11/2021 | Smith | |

(Continued)

FOREIGN PATENT DOCUMENTS

| | | |
|---|---|---|
| EP | 1083643 A2 | 3/2001 |
| EP | 3651290 A1 | 5/2020 |

(Continued)

*Primary Examiner* — Son T Le
(74) *Attorney, Agent, or Firm* — Patterson + Sheridan, LLP

(57) ABSTRACT

Aspects of the present disclosure provide techniques for performing a safety test of a laser diode associated with an ophthalmic surgical apparatus. An example method determining a measured slope efficiency of the laser diode based on a plurality of different current levels applied to an input of the laser diode and a plurality of different output power levels associated with the laser diode, determining an expected slope efficiency of the laser diode based on a measured operating temperature of the ophthalmic surgical apparatus, determining a result of the safety test of the laser diode based on the measured slope efficiency of the laser diode and the expected slope efficiency for the laser diode, and outputting an electrical signal indicating a result of the safety test of the laser diode.

15 Claims, 10 Drawing Sheets

(56)         References Cited

U.S. PATENT DOCUMENTS

| | | | |
|---|---|---|---|
| 2007/0086495 A1 | 4/2007 | Sprague et al. | |
| 2007/0253454 A1 | 11/2007 | Gustavson et al. | |
| 2020/0107960 A1 | 4/2020 | Bacher et al. | |
| 2021/0135424 A1 | 5/2021 | Bacher et al. | |
| 2021/0273399 A1 | 9/2021 | Gerlach et al. | |
| 2022/0110793 A1 | 4/2022 | Sawicz et al. | |
| 2023/0181025 A1 | 6/2023 | Hallen et al. | |

FOREIGN PATENT DOCUMENTS

| | | | |
|---|---|---|---|
| EP | 3893411 A1 | 10/2021 | |
| JP | 2007335597 A | 12/2007 | |
| WO | 2007059258 A1 | 5/2007 | |

* cited by examiner

Temperature

TECHNIQUES FOR PERFORMING A SAFETY TEST OF A LASER DIODE OPHTHALMIC SURGICAL APPARATUS

BACKGROUND

In a wide variety of medical procedures, laser light (e.g., laser treatment beam ("treatment beam"), laser aiming beam ("aiming beam"), etc.) is used to assist in surgery and/or treat patient anatomy. For example, in laser photocoagulation, a laser probe propagates a laser treatment beam to cauterize blood vessels at a burn spot across the retina. A laser treatment beam is typically transmitted from a surgical laser system through an optical fiber that proximally terminates in a port adapter, which connects to the surgical laser system, and distally terminates in the laser probe, which is manipulated by a surgeon. Note that, herein, a distal end of a component refers to the end that is closer to a patient's body while the proximal end of the component refers to the end that is facing away from the patient's body or is in proximity to, for example, the surgical laser system.

In addition to cauterizing blood vessels at the burn spot, the treatment beam may also damage some of the rods and cones that are present in the retina that provide vision, thereby, affecting eyesight. Since vision is most acute at the central macula of the retina, the surgeon arranges the laser probe to generate a burn spot in the peripheral areas of the retina. During the procedure, the surgeon drives the probe with a non-burning aiming beam to illuminate the retinal area that is to be photocoagulated. Due to the availability of low-power red laser diodes, the aiming beam is generally a low-power red laser light. Once the surgeon has positioned the laser probe so as to illuminate a desired retinal spot with the aiming beam, the surgeon activates the laser treatment beam through a foot pedal or other means to photocoagulate the illuminated area (e.g., or an area encompassing the illuminated area) using the laser treatment beam. Having burned a retinal spot, the surgeon repositions the probe to illuminate a new spot with the aiming light, activates the laser treatment beam to photocoagulate the new spot, repositions the probe, and so on until a desired number of burned laser spots are distributed across the retina.

SUMMARY

Certain embodiments pertain to a method for performing a safety test of a laser diode associated with an ophthalmic surgical apparatus. The method may include measuring an operating temperature of the ophthalmic surgical apparatus, outputting a plurality of different current levels and applying the plurality of different current levels to an input of the laser diode, and determining a plurality of different output power levels associated with the laser diode based on the plurality of different current levels applied to the input of the laser diode, wherein the plurality of different output power levels include a different output power for each of the different current levels of the plurality of different current levels. The method may also include determining a measured slope efficiency of the laser diode based on the plurality of different current levels and the plurality of different output power levels, determining an expected slope efficiency of the laser diode based on the measured operating temperature of the ophthalmic surgical apparatus, determining a result of the safety test of the laser diode based on the measured slope efficiency of the laser diode and the expected slope efficiency for the laser diode, and outputting an electrical signal indicating result of the safety test of the laser diode.

In certain embodiments, an apparatus is provided for performing a safety test of a laser diode of an ophthalmic surgical apparatus. The apparatus includes a temperature sensor configured to measure an operating temperature of the ophthalmic surgical apparatus. The apparatus also includes a power module configured to: output a plurality of different current levels, apply the plurality of different current levels to an input of the laser diode, and determine a plurality of different output power levels associated with the laser diode based on the plurality of different current levels applied to the input of the laser diode, wherein the plurality of different output power levels includes a different output power for each of the different current levels of the plurality of different current levels. The apparatus also includes one or more processors configured to: obtain the measured temperature of the ophthalmic surgical apparatus from the temperature sensor, obtain, from the power module, an indication of the plurality of different output power levels and the plurality of different current levels, determine a measured slope efficiency of the laser diode based on the plurality of different current levels and the plurality of different output power levels, determine an expected slope efficiency of the laser diode based on the measured operating temperature of the ophthalmic surgical apparatus, determine a result of the safety test of the laser diode based on the measured slope efficiency of the laser diode and the expected slope efficiency for the laser diode, and output an electrical signal indicating result of the safety test of the laser diode.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

3

Figure 10:
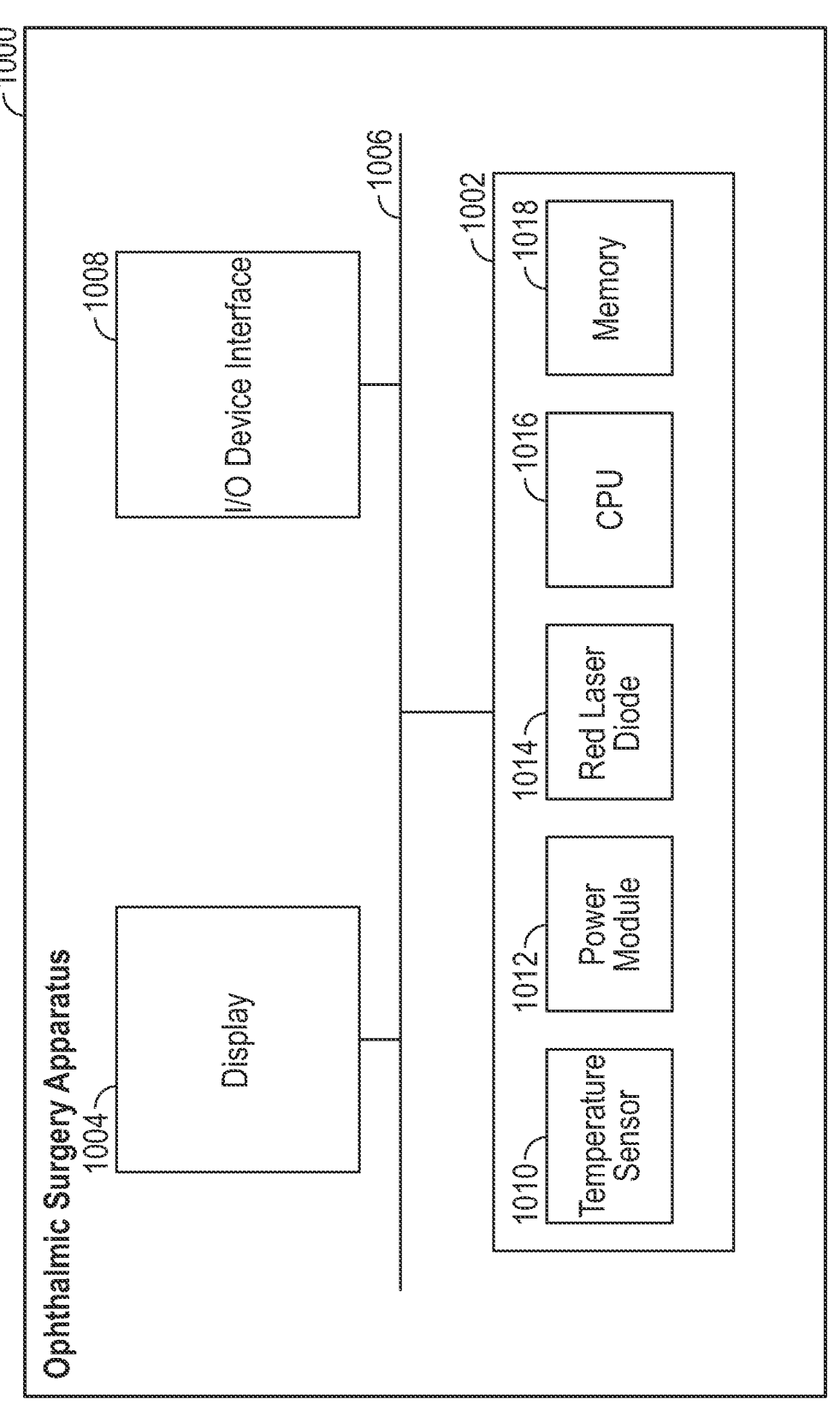

FIG. 10 illustrates an exemplary diagram showing how various components of the ophthalmic surgical apparatus, utilized in conjunction with certain embodiments described herein, communicate and operate together.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

In the following description, details are set forth by way of example to facilitate an understanding of the disclosed subject matter. It should be apparent to a person of ordinary skill in the field, however, that the disclosed implementations are exemplary and not exhaustive of all possible implementations. Thus, it should be understood that reference to the described examples is not intended to limit the scope of the disclosure. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Note that, as described herein, a distal end, segment, or portion of a component refers to the end, segment, or portion that is closer to a patient's body during use thereof. On the other hand, a proximal end, segment, or portion of the component refers to the end, segment, or portion that is distanced further away from the patient's body is in proximity to, for example, a surgical laser system.

As used herein, the term "about" or approximately may refer to a +/−10% variation from the nominal value. It is to be understood that such a variation can be included in any value provided herein.

Example Surgical Laser System

Figure 1:
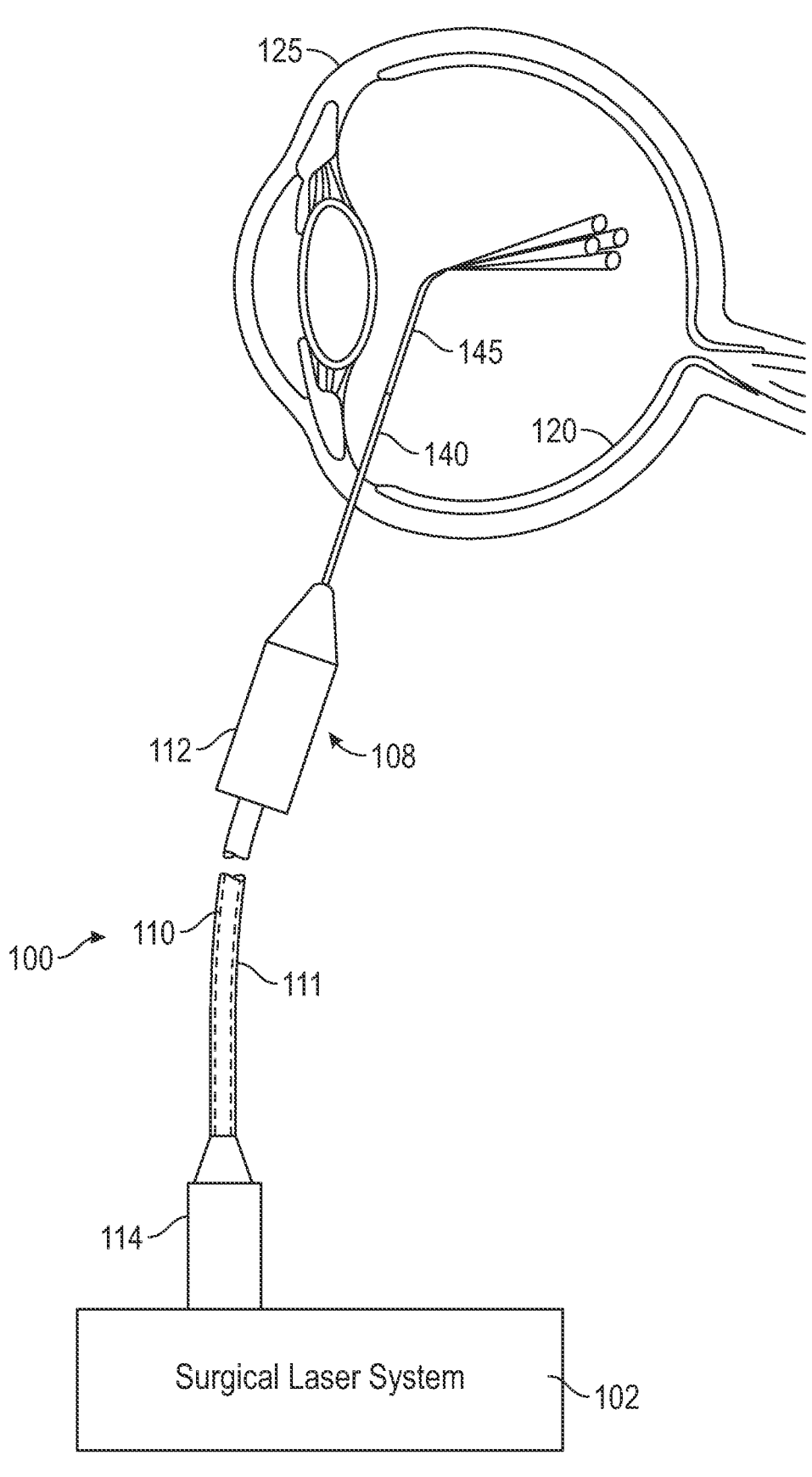
FIG. 1 illustrates a plan view of a system for generating laser beams for delivery to a surgical target, in accordance with certain embodiments of the present disclosure.

FIG. 1 illustrates an example system 100 for performing a laser-assisted ophthalmic procedure, according to certain embodiments. System 100 includes a surgical laser system 102 having one or more laser sources for generating laser beams. For example, a first laser source within surgical laser system 102 may generate a treatment beam with a first wavelength (e.g., ~532 nanometers (nm)) while a second laser source may generate an aiming beam with a second wavelength (e.g., ~635 nm). A user, such as a surgeon, may first trigger the surgical laser system 102 (e.g., via a foot switch, voice commands, etc.) to emit the aiming beam onto a desired retinal spot. Once the surgeon has positioned the laser probe so as to illuminate the desired retinal spot with the aiming beam, the surgeon activates the treatment beam, such as through a foot pedal or other means, to treat patient anatomy (e.g., photocoagulate the desired retinal spot using the treatment beam).

As shown, surgical laser system 102 includes a connector or port adapter 114 that couples to an optical port of surgical laser system 102. FIG. 1 also shows an optical fiber 110 inside an optical fiber cable 111 having a distal end that couples to and extends through a probe 108 and a proximal end that couples to and extends through port adapter 114. In some cases, as further described herein, the optical fiber 110 may include more than one fiber. In the example of FIG. 1, port adapter 114 includes a ferrule with an opening in which the proximal end of optical fiber 110 is inserted. The proximal end of optical fiber 110 includes an interface plane (also referred to as a proximal entrance plane) upon which laser beams from surgical laser system 102 may be focused when the proximal end of optical fiber 110 is inserted into the ferrule. The interface plane of optical fiber 110 comprises the exposed proximal ends of the one or more cores where laser beams may be directed to. In the example of FIG. 1, optical fiber 110 is a multi-core optical fiber (MCF) with four cores. As such, the interface plane of the proximal end of optical fiber 110 comprises the proximal ends of the four cores upon which laser beams may be focused. In some cases, the optical fiber 110 may be a single-core optical fiber with only one core.

Surgical laser system 102 may be configured to split a single laser beam that is generated by a laser source into multiple laser beams that exhibit a laser spot pattern. For example, surgical laser system 102 may split an aiming beam into four aiming beams and then deliver the four aiming beams to the interface plane of optical fiber 110 through the opening of the ferrule of port adapter 114. Surgical laser system 102 may further be configured to split the treatment beam into four treatment beams and deliver the four treatment beams to the interface plane of optical fiber 110 through the opening of the ferrule. In such an example, each of the cores of optical fiber 110 may transmit a multi-wavelength or combined beam, which may refer to a treatment beam combined with an aiming beam. Though certain aspects are described with respect to the cores of the optical fiber transmitting a combined beam, it should be noted that the cores of optical fiber 110 can also individually transmit either the treatment beam or the aiming beam, depending on which beam(s) are activated and incident on the optical fiber 110.

In some examples, surgical laser system 102 may also propagate an illumination beam into an interface plane of optical fiber 110 (e.g., which may also include a proximal end of a cladding that holds the cores within optical fiber 110) in order to illuminate the inside of the eye, especially areas of the retina 120 that are to be photocoagulated. In certain aspects, an illumination beam may be generated by a white light-emitting diode (LED).

Optical fiber 110 delivers the combined beams to probe 108, which propagates a multi-spot pattern (e.g., four spots) of combined beams to the retina 120 of a patient's eye 125. Probe 108 includes a probe body 112 and a probe tip 140 that house and protect the distal end of optical fiber 110. A distal end portion 145 of the probe tip 140 may also contain a lens that focuses the combined beams on the retina 120.

Figure 2:
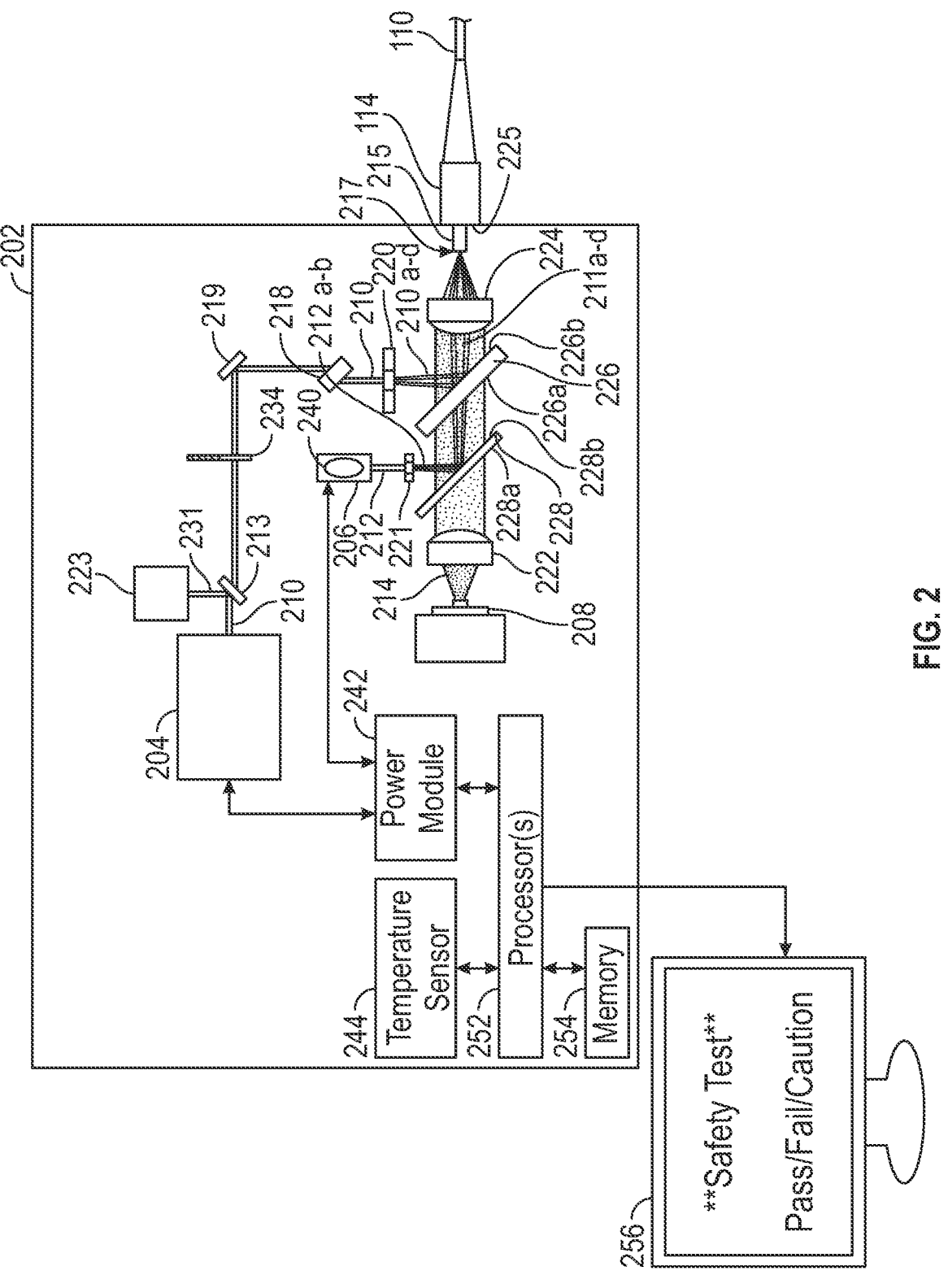
FIG. 2 illustrates an example of a surgical laser system, and the components therein, in accordance with certain embodiments of the present disclosure.

FIG. 2 illustrates an example surgical laser system 202, and the components therein, that may be implemented according to embodiments described herein. Surgical laser system 202 is an example embodiment of surgical laser system 102. Surgical laser system 202 comprises a laser source 204, which propagates a treatment beam 210, laser source 206, which propagates an aiming beam 212, and a light source 208, which propagates an illumination beam 214. Surgical laser system 202 further includes a plurality of lenses, diffractive elements, beam splitters, and other optical relay devices for relaying the laser and illumination beams between their respective sources and desired ports, which may together be referred to as an "optical relay system."

At the outset of the surgery, a surgeon may activate light source 208 in order to illuminate the inside of the eye's globe and make it easier to view the retina. As shown, once emitted by light source 208, illumination beam 214 (stippled segment) is received by collimating lens 222, which is configured to produce a beam with parallel rays of light. In certain embodiments, collimating lens 222 may be a multi-element achromat comprising two singlet lenses and one doublet lens. Therefore, as shown, illumination beam 214 emerges with parallel rays of light from the other side of collimating lens 222 and passes through beam splitters 228 and 226 (which may also be referred to as dichroic mirrors), respectively, to reach a condensing lens 224. In certain embodiments, condensing lens 224 may be a multi-element achromat comprising two singlet lenses and one doublet lens. In such embodiments, condensing lens 224 may have the same design as collimating lens 222, except that the assembly is reversed (e.g., rotated by 180 degrees), thereby creating a one-to-one magnification imaging system. Each of beam splitters 228 and 226 may have different coatings on their two sides, 228a and 228b, and 226a and 226b, respectively. For example, sides 228a and 226a are coated such that they allow light propagated thereon to pass through beam splitters 228 and 226. As such, a substantial portion of illumination beam 214, which is propagated onto sides 228a and 226a passes beam splitters 228 and 226. On the other hand, sides 228b and 226b are coated to reflect light or laser beams such as aiming beam 212 and treatment beam 210, respectively, as further described below.

Condensing lens 224 then converges illumination beam 214 into an interface plane of a proximal end of an optical fiber, such as optical fiber 110, which is coupled to port 225 of surgical laser system 202 through port adapter 114. As described in relation to FIG. 1, optical fiber 110 may have four cores in a 2×2 array embedded within a larger-diameter cylindrical cladding. As such, condensing lens 224 focuses illumination beam 214 into an interface plane of optical fiber 110 such that illumination beam 214 is propagated, along an entire length and through an entire diameter of the cladding and each of the four cores of optical fiber 110, to the distal end of a surgical probe (e.g., probe 108 of FIG. 1) that is coupled to optical fiber 110. As described above, the interface plane of optical fiber 110 comprises the proximal ends of the four cores and cladding thereof that are exposed through opening 217 of port adapter 114, respectively, via ferrule 215.

Once the surgeon is able to view inside the eye's globe, the surgeon may project from the distal end of the probe one or more desired aiming beam spots onto the retina. More specifically, after activation by the surgeon, laser source 206 emits aiming beam 212, e.g., a red laser beam, onto diffraction optical element (DOE) 221. A diffraction segment may also be referred to as a "segment" herein. In the example of FIG. 2, DOE 221 is positioned such that aiming beam 212 is aligned with the middle segment of DOE 221, which diffracts aiming beam 212 into aiming beams 212a-d (e.g., four aiming beams). However, a surgeon may change the position of DOE 221 in order to diffract a beam into a different number of beams (e.g., 2 or 1). For example, using voice command or some other feature of surgical laser system 202, a surgeon may position DOE 221 to align aiming beam 212 with a different segment of DOE 221, which may diffract aiming beam 212 into two or one or other numbers of beams.

Once diffracted, the resulting aiming beams are reflected by beam splitter 228 through beam splitter 226 and onto condensing lens 224. In examples where aiming beams 212a-d are red aiming beams, beam splitter 228 may be a red dichroic optical element, and aiming beams 212a-d may reflect off of a narrowband red spectral notch in beam splitter 228. Condensing lens 224 then focuses the four aiming beams onto the interface plane of a proximal end of optical fiber 110 such that each of the aiming beams is propagated, along an entire length of a corresponding core of optical fiber 110, to the distal end of a surgical probe (e.g., probe 108 of FIG. 1). Each of the four aiming beams focuses with high coupling efficiency into the corresponding core within the 4-core MCF, and propagated down the length of the core to the distal end of the MCF. This allows the surgeon to project from the distal end of the probe four desired aiming beam spots onto the retina.

As described above, once the surgeon has positioned and activated the laser probe so as to project aiming beam spots onto the retina, the surgeon activates laser source 204, such as through a foot pedal or other means, to treat patient anatomy (e.g., photocoagulate the desired retinal spot using the treatment beam). When activated, laser source 204 emits treatment beam 210 (e.g., a green laser beam) as shown in FIG. 2. The treatment beam 210 reaches beam splitter 213, which is configured to allow a substantial portion of treatment beam 210 to pass through, while reflecting a trivial portion 231 onto sensor 223. Sensor 223 is a light sensor configured to detect whether laser source 204 is active or not and to monitor the treatment beam power. After passing through beam splitter 213 and provided that a shutter 234 is in an open position to permit the treatment beam 210, treatment beam 210 is received at fixed fold mirror 219, which is configured to reflect treatment beam 210 onto beam splitter 218.

As noted, the surgical laser system 202 may also include the shutter 234 arranged between the laser source 204 and the fixed fold mirror 219. The shutter 234, may be configured to alternatively block or permit the treatment beam 210 from reaching the fixed fold mirror 219. A surgeon or surgical staff member can control the shutter 234 (e.g., via a foot switch, voice commands, etc.) to emit the laser aiming beam and fire the treatment laser beam (e.g., open the shutter 234) to treat patient anatomy (e.g., to perform photocoagulation). In each case, the beam splitter 218 may direct the laser beams towards the port adapter 114.

As shown, the treatment beam 210 passes through beam splitter 218 before reaching DOE 220. DOE 220, similar to DOE 221, then diffracts treatment beam 210 into treatment beams 210a-210d (e.g., four treatment beams). However, a surgeon may change the position of DOE 220 in order to diffract a beam into a different number of beams (e.g., 2 or 1). For example, using voice command or some other feature of surgical laser system 202, a surgeon may position DOE 220 to align treatment beam 210 with a different segment of DOE 220, which may diffract treatment beam 210 into two or one or other numbers of beams. In some cases, the 2×2 array of four red laser aiming beams 212a-d and the 2×2 array of four green laser treatment beams 210a-210 may be coupled into and confined within the four cores without spilling over into the surrounding cylindrical cladding.

Treatment beams 210a-210d are then received at beam splitter 226, which reflects treatment beams 210a-210d onto condensing lens 224. In examples where treatment beams 210a-d are green treatment beams, beam splitter 226 may be a green dichroic optical element, and treatment beams 210a-d may reflect off of a narrowband green spectral notch in beam splitter 226. Treatment beams 210a-d are reflected by beam splitter 226 at an angle with respect to beam splitter 226 that is equal to the angle with which aiming beams 212a-d are passed through beam splitter 226. Therefore, when laser source 204 is active, transmitted treatment beams 210*a-d* and aiming beams 212*a-d* are combined (e.g., such that they overlay each other) creating combined beams 211*a-d*, before reaching condensing lens 224.

Condensing lens 224 focuses combined beams 211*a*-211*d* onto an interface plane of the proximal end of optical fiber 110 such that each of the combined beams 211*a*-211*d* is propagated, along an entire length of a corresponding core of optical fiber 110, to the distal end of a surgical probe (e.g., probe 108 of FIG. 1). More specifically, in the example of FIG. 2, optical fiber 110 is an MCF with four cores, such as cores A, B, C, and D. In such an example, condensing lens 224 focuses combined beams 211*a*-211*d* onto an interface plane of a proximal end of optical fiber 110 such that, for example, combined beam 211*a* is propagated onto core A, combined beam 211*b* is propagated onto core B, combined beam 211*c* is propagated onto core C, and combined beam 211*d* is propagated onto core D. While FIG. 2 illustrates an embodiment for splitting a treatment beam 210 into four treatment beams 210*a-d* and focusing each of the treatment beams 210*a-d* onto separate cores, it should be understood that only one treatment beam may be used and focused on to a single core optical fiber. Similarly, while FIG. 2 illustrates an embodiment for splitting an aiming beam 212 into four aiming beams 212*a-d* and focusing each of the aiming beams 212*a-d* onto separate cores, it should be understood that only one aiming beam may be used and focused on to a single core optical fiber.

Additionally, as shown, the surgical laser system 202 of FIG. 2 includes a temperature sensor 244 configured to monitor/sense a temperature of the surgical laser system 202, one or more processors 252 configured to retrieve and execute programming instructions stored in a memory 254 for operating one or more components of the surgical laser system 202, and a power module 242 configured to power one or more components of the surgical laser system 202 (e.g., the laser source 204, the laser source 206, etc.). Additionally, FIG. 2 includes a display 256 configured to display information output by the surgical laser system 202 of FIG. 2. Additional aspects regarding the temperature sensor 244, the one or more processors 252, the memory 254, the power module 242, and the display 256 are described below.

Aspects Related to Performing a Safety Test of a Laser Diode in an Ophthalmic Surgical Apparatus As noted above, the surgical laser system 202 of FIG. 2 includes the laser source 206 that propagates the aiming beam 212. In some cases, the laser source 206 may comprise a red laser diode 240, which may be subject to laser classification limit for eye safety purposes. For example, the red laser diode 240 may be subject to a class 2 laser limit, limiting output of the red laser diode 240 to one milliwatts (mW) continuous wave output power accessible to the human eye. In some cases, to help ensure that an emitted power of the red laser diode 240 does not exceed a maximum power level for class 2 lasers (e.g., one mW), the surgical laser system 202 includes a power module 242. For example, the power module 242 may be configured to measure a radiometric output power of the red laser diode 240 based on a portion of the aiming beam 212 and to adjust, based on the measured output power, a power supplied to the red laser diode 240 so that the red laser diode 240 does not exceed the maximum power level for class 2 lasers.

While the above approach may help to avoid situations in which the radiometric output power of the red laser diode 240 exceeds the maximum power level, these approaches rely on the power module 242 never malfunctioning. However, if the power module 242 does malfunction, and if it malfunctions in such a way that that the emitted power of the red laser diode 240 appears to be much less than the actual emitted power of the red laser diode 240, this scenario may create a dangerous looping situation in which the power module 242 responds by increasing a current/power supplied to the red laser diode 240 to compensate for seemingly low power, resulting in the output power of the red laser diode 240 being driven much higher than the permitted maximum power level.

In some cases, to avoid situations in which the power module 242 malfunctions and the output power of the red laser diode 240 exceeds the maximum power level, a backup system could be created that relies on (1) capping the current to the red laser diode 240 and (2) tightly controlling the temperature of the red laser diode 240. However, one issue with this type of system is that (a) controlling current is a poor way to control output power without tightly controlling temperature, as explained above, and (b) tightly controlling the diode temperature is complicated and expensive.

Figure 3:
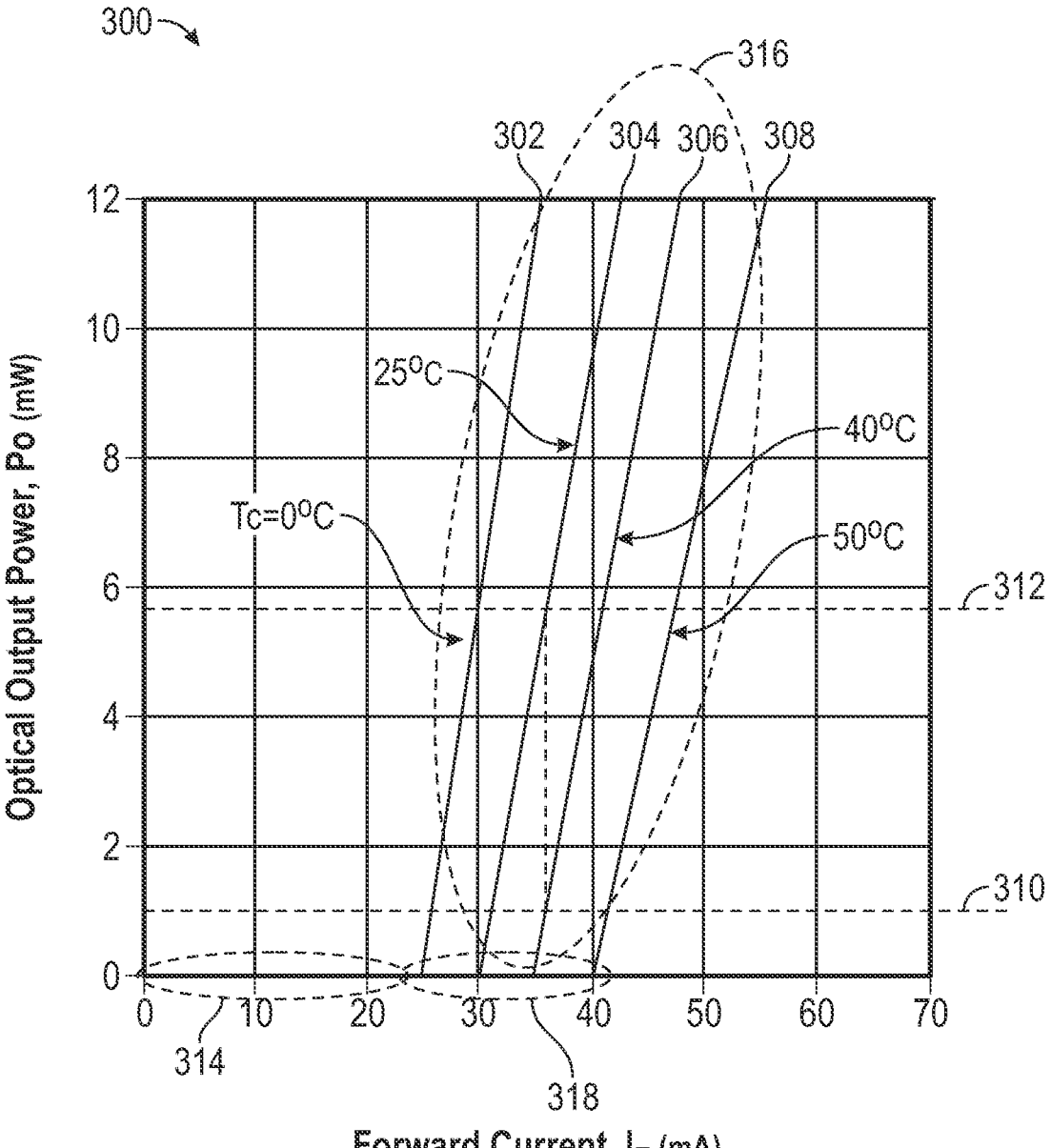
FIG. 3 illustrates a graph including a plurality of curves plotting an optical output power versus forward current for a red laser diode for different temperatures.

For example, FIG. 3 illustrates a graph 300 including a plurality of curves 302-308 plotting an optical output power versus forward current for the red laser diode 240 for different temperatures, such as 0° C., 25° C., 40° C., and 50° C. The red laser diode output power versus forward current has a characteristic hockey-stick shape, with three distinct zones: (1) a light emitting diode (LED) zone 314 in a low-current region, where the red laser diode 240 is not yet lasing but is emitting incoherent LED light, and where the linear increase of output power versus forward current is low, (2) a lasing zone 316 in a high current region, where the diode is lasing and where the linear increase of output power versus forward current is high, and (3) a transition zone 318 between the LED zone 314 and the lasing zone 316 that is typically narrow, over a small forward current range. As shown in FIG. 3, a slope of the LED zone 314 appears to be zero and the transition zone 318 appears to have zero current width. However, the slope of the LED zone 314 is non-zero but very small. Likewise, the current width of the transition zone 318 is also non-zero but very small.

As shown on curve 306 in FIG. 3, for the temperature of 40° C., supplying the red laser diode 240 with a forward current of approximately 35 milliamps (mA) results in an output power of the red laser diode 240 at the maximum power level of 1 mW shown at 310. However, supplying this same amount of forward current (e.g., 35 mA) when the temperature is lower than 40° C. will result in the output power of the red laser diode 240 exceeding the maximum power level of 1 mW. For example, as shown on curve 304, supplying the red laser diode 240 with 35 mA at a temperature of 25° C. produces, as shown at 312, an output power of the red laser diode 240 of nearly 6 mW, resulting in the red laser diode 240 no longer being classified as a class 2 laser and potentially causing eye damage.

Accordingly, as can be seen in FIG. 3, minor fluctuations in operating temperature can cause the output power of the red laser diode 240 to fluctuate significantly. In some cases, these fluctuations in temperature can occur, for example, when the surgical laser system 202 is powered on and begins to heat up due to heat dissipation of various components of the surgical laser system 202. Moreover, part-to-part laser diode variability may cause each red laser diode to have a different, unique output power versus forward current relationship so that a current and temperature that maintains the output power below the maximum power level for one red laser diode may allow the output power to greatly exceed the maximum power level for a different red laser diode.

Accordingly, aspects of the present disclosure provide techniques for reducing the probability that a laser diode of an ophthalmic surgical apparatus, such as the red laser diode 240 in the surgical laser system 202, is accidentally operated above a maximum power level of the laser diode. In some cases, these techniques may involve performing a safety test of the laser diode of the ophthalmic surgical apparatus to determine whether the laser diode is safe to use. In some cases, to avoid the temperature variability associated with the forward current and output power of laser diodes described above, the safety test may take into account a slope efficiency of the laser diode (e.g., a change in the output power of the laser diode divided by a change in the forward current of the laser diode), which may not be as susceptible to variation due to temperature changes.

Figure 4:
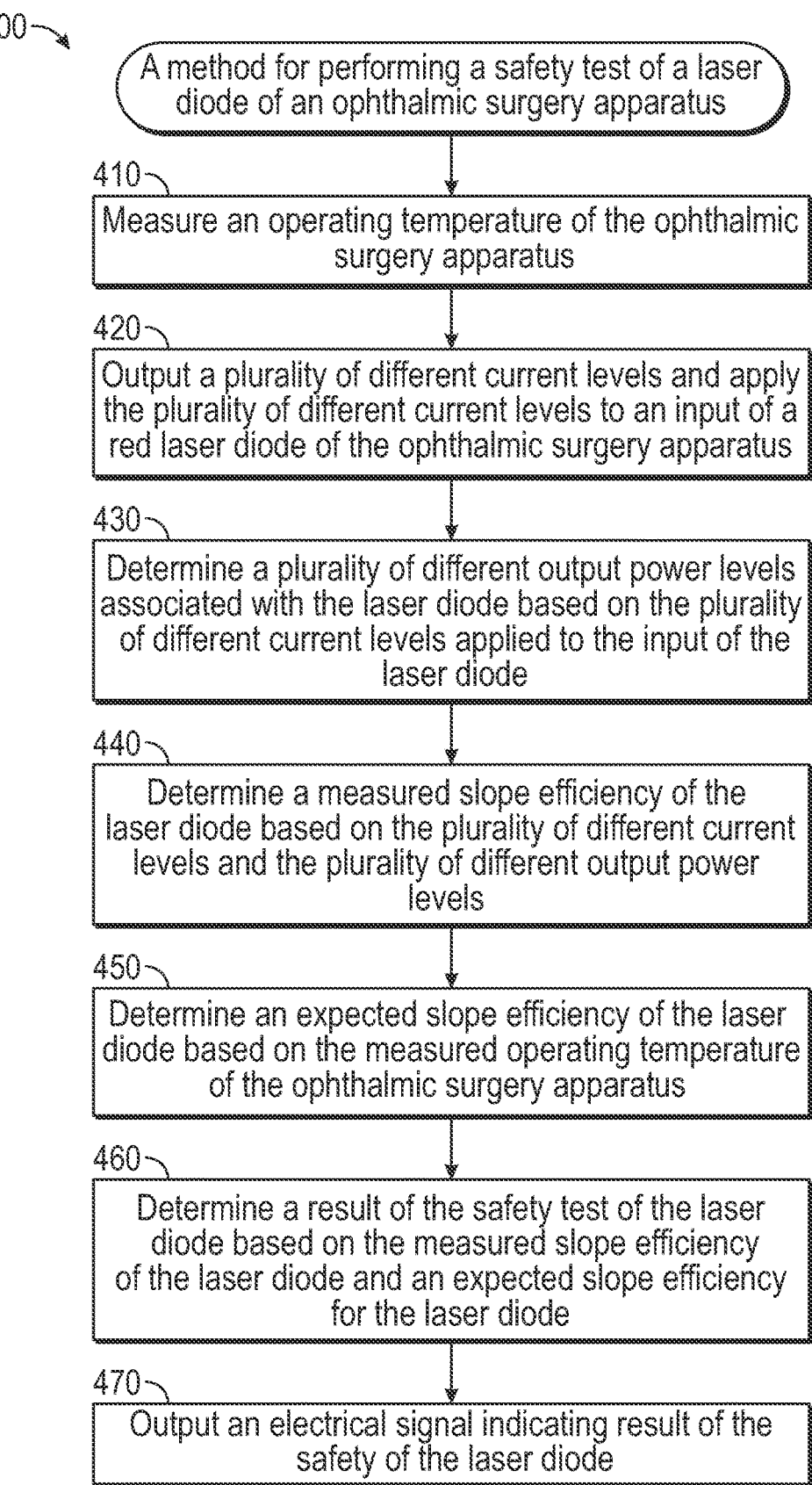
FIG. 4 illustrates an example process for performing a safety test of a laser diode of an ophthalmic surgical apparatus.

Example Operations for Performing a Safety Test Associated with a Laser Diode FIG. 4 illustrates an example process 400 for performing a safety test of a laser diode of an ophthalmic surgical apparatus, such as the red laser diode 240 of the surgical laser system 202.

The process 400 begins at 410 with measuring an operating temperature of the surgical laser system 202. In some cases, the surgical laser system 202 may measure the temperature using a temperature sensor, such as a temperature sensor 244 of the surgical laser system 202 shown in FIG. 2.

At 420, the surgical laser system 202 outputs a plurality of different current levels (e.g., 10 mA, 12 mA, 14 mA, 16 mA, and 18 mA) and applies the plurality of different current levels to an input of the red laser diode 240. For example, in some cases, the power module 242 may include a digital to analog converter (DAC) configured to output and apply the plurality of different current levels to the input of the red laser diode 240 in response to different voltage levels applied to the DAC. In some cases, the power module 242 may include an internal ammeter that may be configured to measure the plurality of different current levels being applied to the input of the red laser diode 240.

At 430, the surgical laser system 202 determines a plurality of output power levels associated with the red laser diode 240 based on the plurality of different current levels applied to the input of the red laser diode 240. In some cases, the plurality of output power levels include a different output power for each of the plurality of different current levels. In some cases, in order to determine the plurality of different output power levels associated with the laser diode, the power module 242 of the surgical laser system 202 may be configured to measure a plurality of output voltage levels associated with the red laser diode 240. In such cases, each of the plurality of output voltage levels may correspond to a different current level of the plurality of different current levels applied by the power module 242 to the input of the red laser diode 240.

The power module 242 may then convert the plurality of output voltage levels to the plurality of different output power levels based on the plurality of different current levels applied to the input of the red laser diode 240 and correlation data stored in the memory 254 of the surgical laser system 202 that indicates a correlation between an output voltage level and an output power level of the red laser diode 240. For example, during calibration of the surgical laser system 202, an output voltage level of the red laser diode 240 may be correlated with an output power level of the red laser diode 240 by comparing a measured voltage of the red laser diode 240 with the output power of the red laser diode 240 for two or more different input current levels. Thereafter, interpolation may be performed using the measured voltage and output power for the two or more different input current levels to yield the conversion or correlation between the voltage level and an output power level of the red laser diode 240. Accordingly, during the safety test, the power module 242 may use the correlation data stored in the memory 254 to convert the plurality of output voltage levels to the plurality of different output power levels for the plurality of different current levels applied to the input of the red laser diode 240.

The power module 242 may know the current level (I) applied to the input of the red laser diode 240 and the measured output voltage level (V) corresponding to this applied current level. As such, the power module 242 may use the equation $P=I*V$ to determine the output power level of the red laser diode 240 for a given current level applied to the input of the red laser diode 240.

Thereafter, at 440 of FIG. 4, the surgical laser system 202 determines a measured slope efficiency of the red laser diode 240 based on the plurality of different current levels and the plurality of different output power levels. In some cases, the measured slope efficiency of the red laser diode 240 may be determined by one or more processors 252 of the surgical laser system 202. For example, the one or more processors 252 may obtain, from the power module 242, an indication of the plurality of different output power levels and the plurality of different current levels. The one or more processors may then determine the measured slope efficiency of the red laser diode 240 based on the plurality of different current levels and the plurality of different output power levels.

Figure 5:
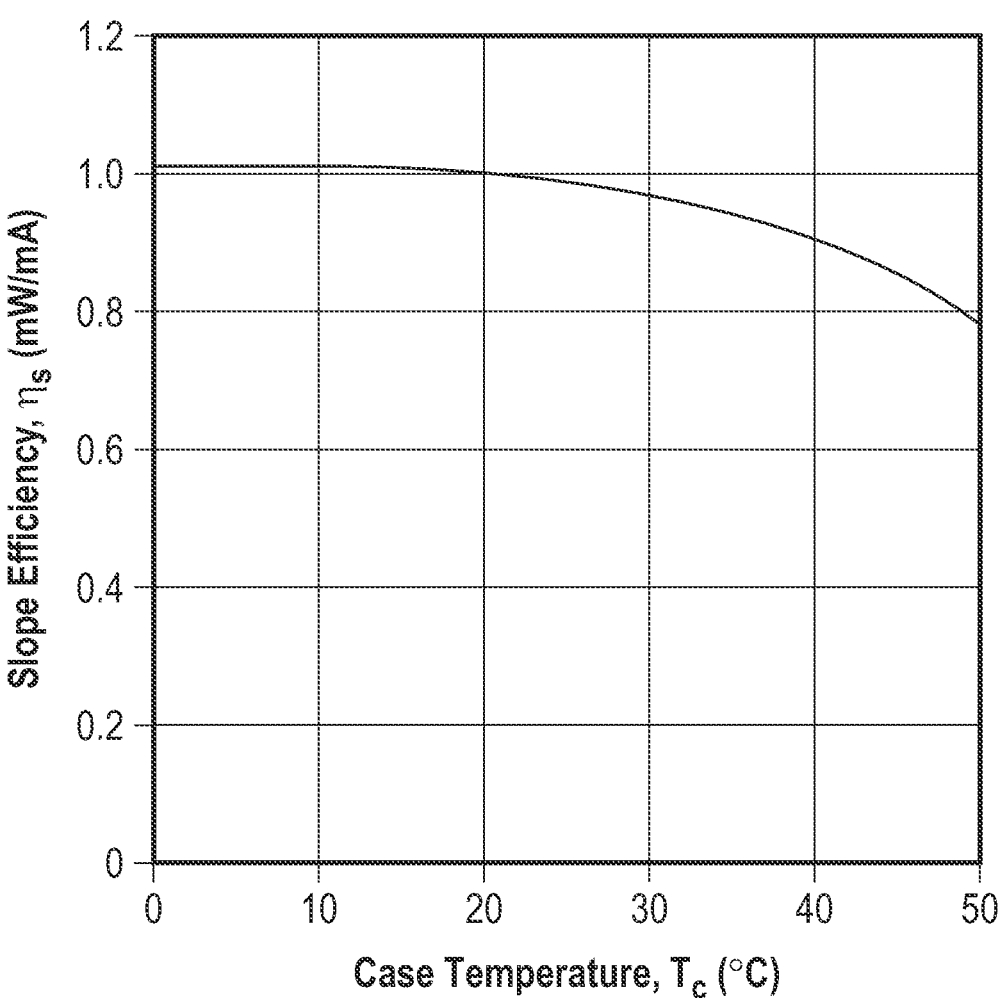
FIG. 5 includes a graph illustrating a slope efficiency versus temperature relationship for the red laser diode, according to certain embodiments.

As noted above, in contrast to the relationship of forward current versus output power of the red laser diode 240, a slope efficiency of the red laser diode 240 (e.g., a change in the output power of the red laser diode 240 divided by change in the forward current of the red laser diode 240) may not be as susceptible to variation due to temperature changes. For example, FIG. 5 includes a graph 500 illustrating a slope efficiency (e.g., mW/mA) versus temperature $(T_C)$ relationship for the red laser diode 240. As shown, the slope efficiency $(S_1)$ remains relatively the same for operating temperatures between 0° C. and 30° C. Due to the relative stability of the slope efficiency for varying operating temperatures associated with the red laser diode 240 (e.g., in contrast to forward current versus output power relationship of the red laser diode 240), performing a safety test of the red laser diode 240 based on the slope efficiency is more reliable.

As noted above, the slope efficiency of the red laser diode 240 represents a change in the output power of the red laser diode 240 divided by change in the forward current of the red laser diode 240. Accordingly, in some cases, in order to determine the measured slope efficiency of the laser diode, the one or more processors 252 may be configured to determine a first difference between the plurality of different output power levels and to determine a second difference between the plurality of different current levels. Thereafter, the one or more processors 252 may determine a ratio of the first difference and the second difference. The measured slope efficiency determined by the one or more processors 252 comprises the determined ratio between the first difference and the second difference.

As an example, assume that the power module 242 applies two current levels (e.g., $I_1$ and $I_2$) to the input of the red laser diode 240 and determines two output power levels (e.g., $P_1$ and $P_2$) corresponding to the two current levels. In this example, the one or more processors 252 may determine the slope efficiency ($S_1$) of the red laser diode 240 at the operating temperature and time (t) as $$S_1(t, T) = \frac{P_2 - P_1}{I_2 - I_1}.$$

Thereafter, at 450, the surgical laser system 202 determines an expected slope efficiency of the red laser diode 240 based on the measured operating temperature (T) and one or more calibration parameters associated with when the red laser diode 240 was originally calibrated.

For example, the one or more processors 252 may be configured to determine the expected slope efficiency of the red laser diode 240 based further on a calibration temperature ($T_{cal}$) associated with when the red laser diode 240 was originally calibrated (e.g., during manufacturing of the surgical laser system 202), a calibration slope efficiency ($S_{cal}$) associated with when the red laser diode 240 was originally calibrated, and one or more aging correction factors.

For example, during calibration of the surgical laser system 202, the calibration temperature ($T_{cal}$) and the calibration slope efficiency ($S_{cal}$) may be recorded and stored in memory 254 of the surgical laser system 202. In some cases, the calibration temperature ($T_{cal}$) and the calibration slope efficiency ($S_{cal}$) may be measured for an LED zone associated with the red laser diode 240, such as the LED zone 314 illustrated in FIG. 3. In some cases, a relationship between slope efficiency and temperature for the red laser diode 240 at time zero (e.g., when the surgical laser system 202 is being calibrated) based on $S_{cal}$ and $T_{cal}$ is shown in Equation 1, below.

$$S(0, T) = S_o T = S_{cal} + S_o'(T - T_{cal}) \tag{1}$$

As shown, Equation 1 includes another parameter known as the "slope of the slope efficiency"

$$(S_o'),$$

which is a measure of a rate of change of the slope efficiency with temperature of the red laser diode 240. The slope of the slope efficiency $$(S_o')$$

may comprise an average slope of the slope term $$(S_{o-ave}')$$

established based on experimental data associated with the surgical laser system 202 (e.g., approximately −0.0287 μW/mA/° C.) and a slope of the slope uncertainty standard deviation term $$(\sigma_{S_o'})$$

also established based on experimental data associated with the surgical laser system 202 (e.g., approximately 0.002481 μW/mA/° C.). The effect of the slope of the slope efficiency on the relationship between the slope efficiency and temperature relationship is illustrated in FIG. 6.

Figure 6:
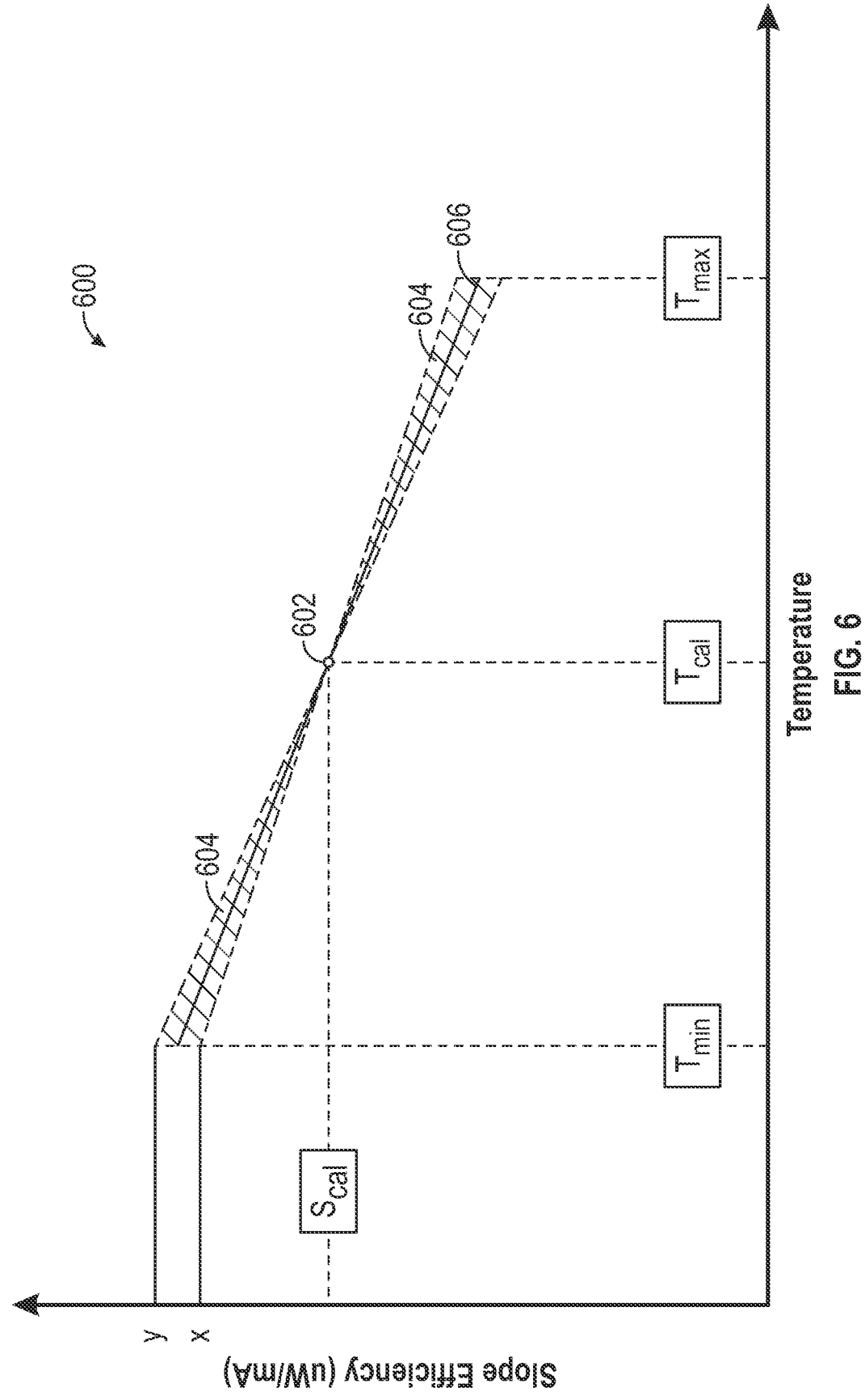
FIG. 6 includes a graph illustrating the slope efficiency versus temperature relationship for the red laser diode, according to certain embodiments.

For example, FIG. 6 includes a graph 600 illustrating the slope efficiency and temperature relationship for the red laser diode 240 based on Equation 1. As shown, FIG. 6 includes a data point 602 representing the calibration temperature ($T_{cal}$) and the calibration slope efficiency ($S_{cal}$) recorded during calibration of surgical laser system 202. Based on $T_{cal}$ and $S_{cal}$, the expected slope efficiency of red laser diode 240 may be extrapolated by using Equation 1 for a range of different temperatures between a minimum operating temperature ($T_{min}$) and a maximum operating temperature ($T_{max}$). In FIG. 6, the curve 606 represents an average expected slope efficiency for the red laser diode 240 for a given temperature. Further, the average expected slope efficiency for the red laser diode 240 for a given temperature may vary slightly due to the uncertainty term of the slope of the slope efficiency $$(S_o')$$

parameter of Equation 1, resulting in an area 604 representing a range of possible expected slope efficiency values for different temperatures. For example, as shown in FIG. 6, given $T_{cal}$ and $S_{cal}$, for the minimum operating temperature ($T_{min}$), the expected slope efficiency of the red laser diode 240 may range between slope efficiency X and slope efficiency Y based on Equation 1.

Figure 7:
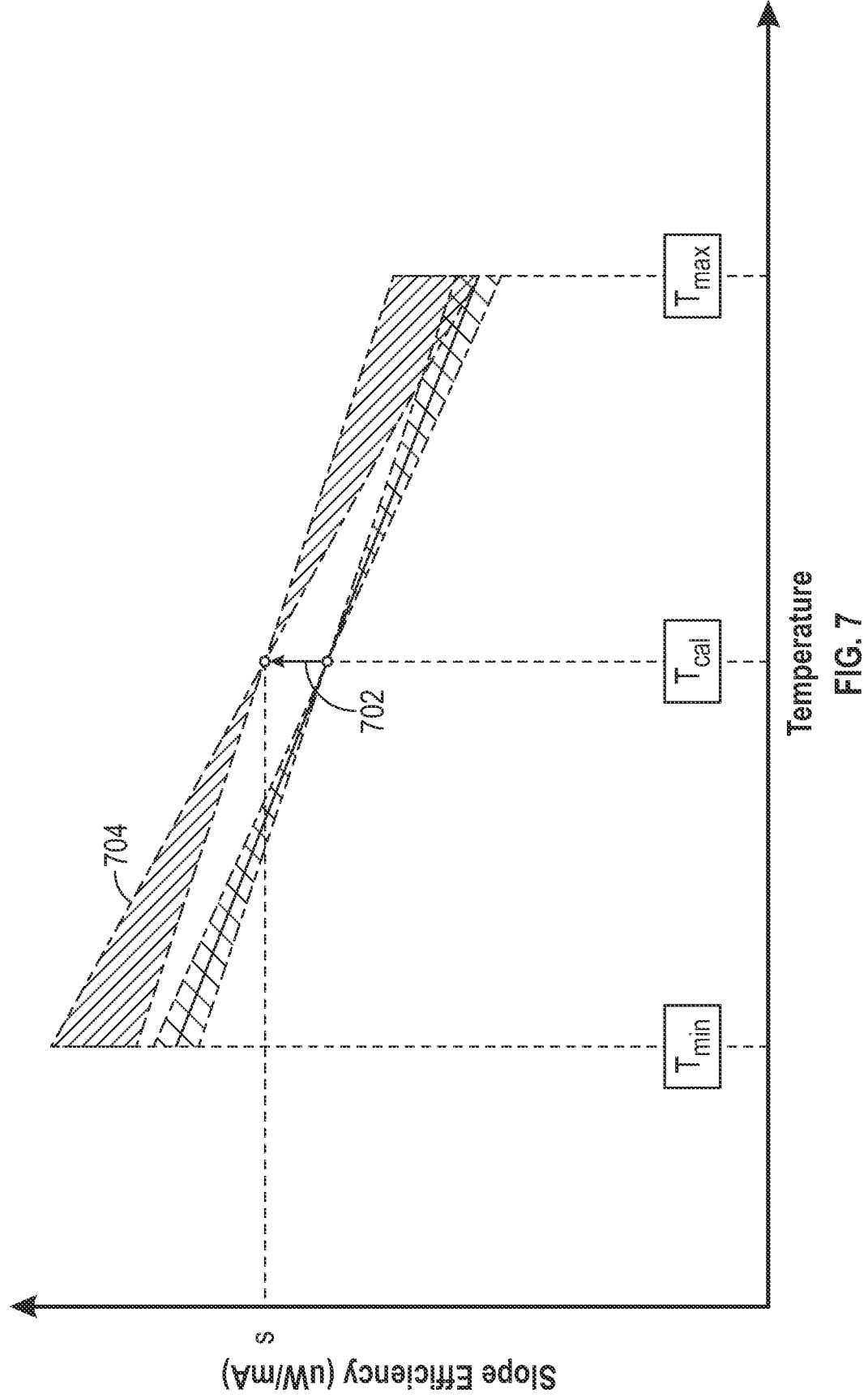
FIG. 7 includes a graph illustrating effects of aging on the slope efficiency versus temperature relationship for the red laser diode, according to certain embodiments.

In some cases, the relationship between slope efficiency of the red laser diode 240 and temperature may change over time as the red laser diode ages. For example, as shown in FIG. 7, the slope efficiency (S) at $T_{cal}$ for the red laser diode 240 tends to increase (but can also slightly decrease) over time as shown at 702 while the slope of the slope efficiency $$(S_o')$$

tends to become more steeply negative as shown at 704. To help correct for the effects of aging on the relationship between slope efficiency of the red laser diode 240 and temperature, a plurality of aging correction factors may be added to Equation 1, as shown below in Equation 2.

$$S(t, T) = S_{cal} \cdot (1 + C) + (1 + R) \cdot S_o' \cdot (T - T_{cal}) \tag{2}$$

In some cases, the one or more processors 252 of the surgical laser system 202 may use Equation 2 at 450 of FIG. 4 to determine the expected slope efficiency of the red laser diode 240 at time t (e.g., a time since the red diode's start of life at which the safety test of the red laser diode 240 is performed) and temperature T (e.g., the operating temperature measured at 410 during the safety test). As shown, Equation 2 includes two aging correction factors: a first aging correction factor (C) and a second aging correction factor (R). The first aging correction factor (C) is applied to the calibration slope efficiency (e.g., the slope efficiency measured during calibration, $S_{cal}$) and corrects for the effects of aging on the slope efficiency of the red laser diode 240, such as the increased slope efficiency as shown at 702 in FIG. 7. A C value of 0 would be when no correction to the slope efficiency measured during calibration is needed. The second aging correction factor (R) is applied to the slope of the slope efficiency ($S_o'$) and corrects for the effects of aging on the slope of the slope efficiency ($S_o'$) associated with the red laser diode 240, such as the steeply negative slope shown at 704 in FIG. 7. In some cases, the first aging correction factor (C), the second aging correction factor (R), and the slope of the slope efficiency ($S_o'$) may be stored in the memory 254 of the surgical laser system 202.

In some cases, to account for uncertainties associated with the first aging correction factor (C), the second aging correction factor (R), and the slope of the slope efficiency ($S_o'$), the one or more processors 252 of the surgical laser system 202 may be further configured to determine a range of the expected slope efficiency of the red laser diode 240. For example, in some cases, the range of the expected slope efficiency of the laser diode may comprise a number of standard deviations above and below the expected slope efficiency of the red laser diode 240, such as two or three standard deviations, resulting in a maximum expected slope efficiency ($S_{max}$) and a minimum expected slope efficiency ($S_{min}$).

Figure 8:
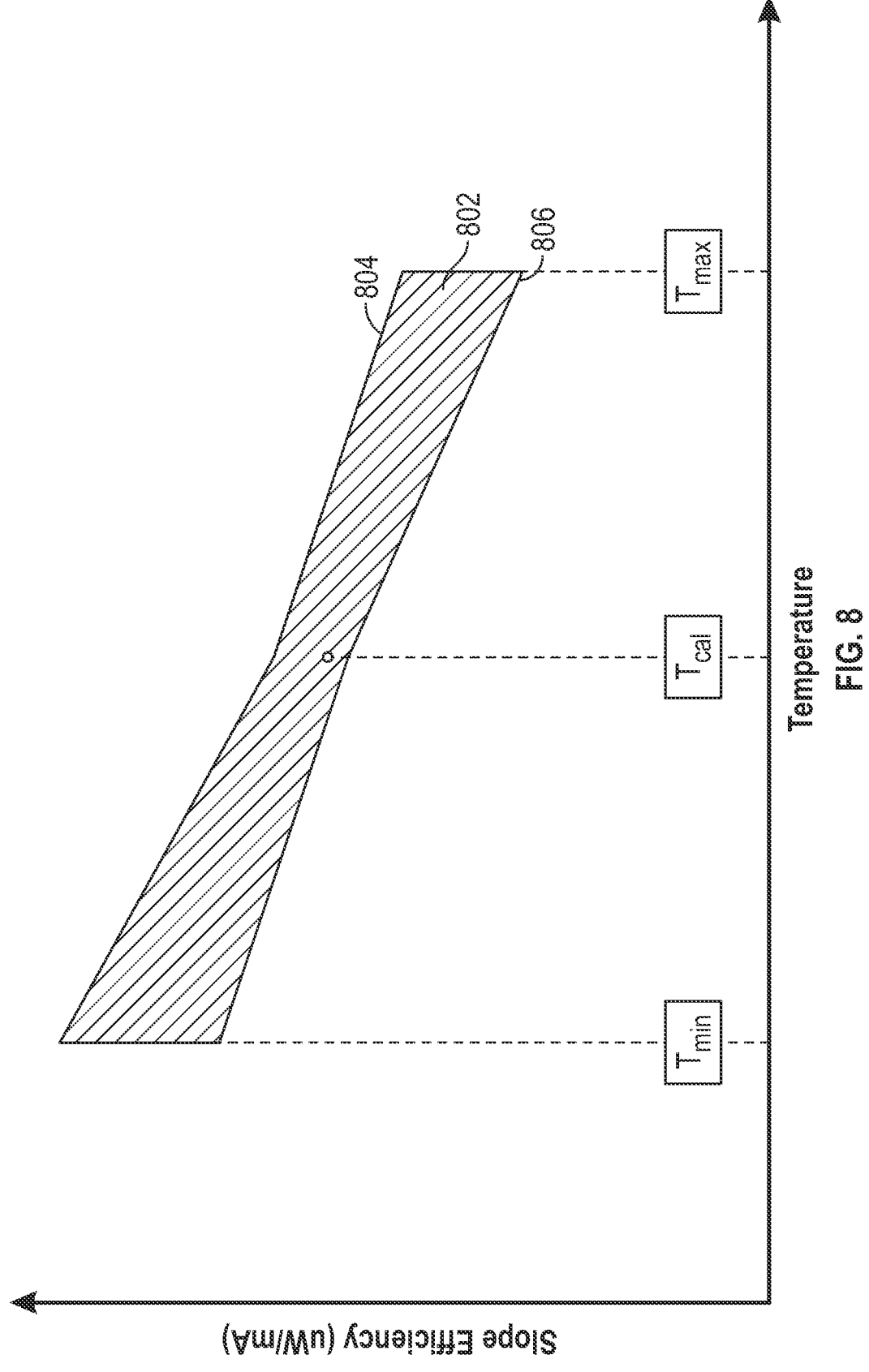
FIG. 8 illustrates an area in which a slope efficiency of the red laser diode is expected to fall within, according to certain embodiments.

As shown in FIG. 8, the range of the expected slope efficiency for the red laser diode 240 may be extended for different temperatures (e.g., ranging between $T_{min}$ and $T_{max}$) using Equation 2 to generate an area 802 in which an actual slope efficiency of the red laser diode 240 (e.g., the measured slope efficiency determined at 440 of FIG. 4) is expected to fall within. In FIG. 8, the boundary line 804 represents the maximum expected slope efficiency ($S_{max}$) for the red laser diode 240 for a given temperature ranging between $T_{min}$ and $T_{max}$ and may be determined by adding the number of standard deviations to the expected slope efficiency of the red laser diode 240 for the given temperature. Similarly, the boundary line 806 represents the minimum expected slope efficiency ($S_{min}$) for the red laser diode 240 for the given temperature ranging between $T_{min}$ and $T_{max}$ and may be determined by subtracting the number of standard deviations from the expected slope efficiency of the red laser diode 240 for the given temperature.

Returning now to FIG. 4, at 460, the surgical laser system 202 determines a result of the safety test of the red laser diode 240 based on the measured slope efficiency of the red laser diode 240 determined at 440 and the expected slope efficiency for the red laser diode 240 determined at 450. Thereafter at 470, the surgical laser system 202 outputs an electrical signal indicating result of the safety of the laser diode. For example, in some cases, the electrical signal may be output by the one or more processor 252 and displayed on a display 256 associated with the surgical laser system 202.

Figure 9:
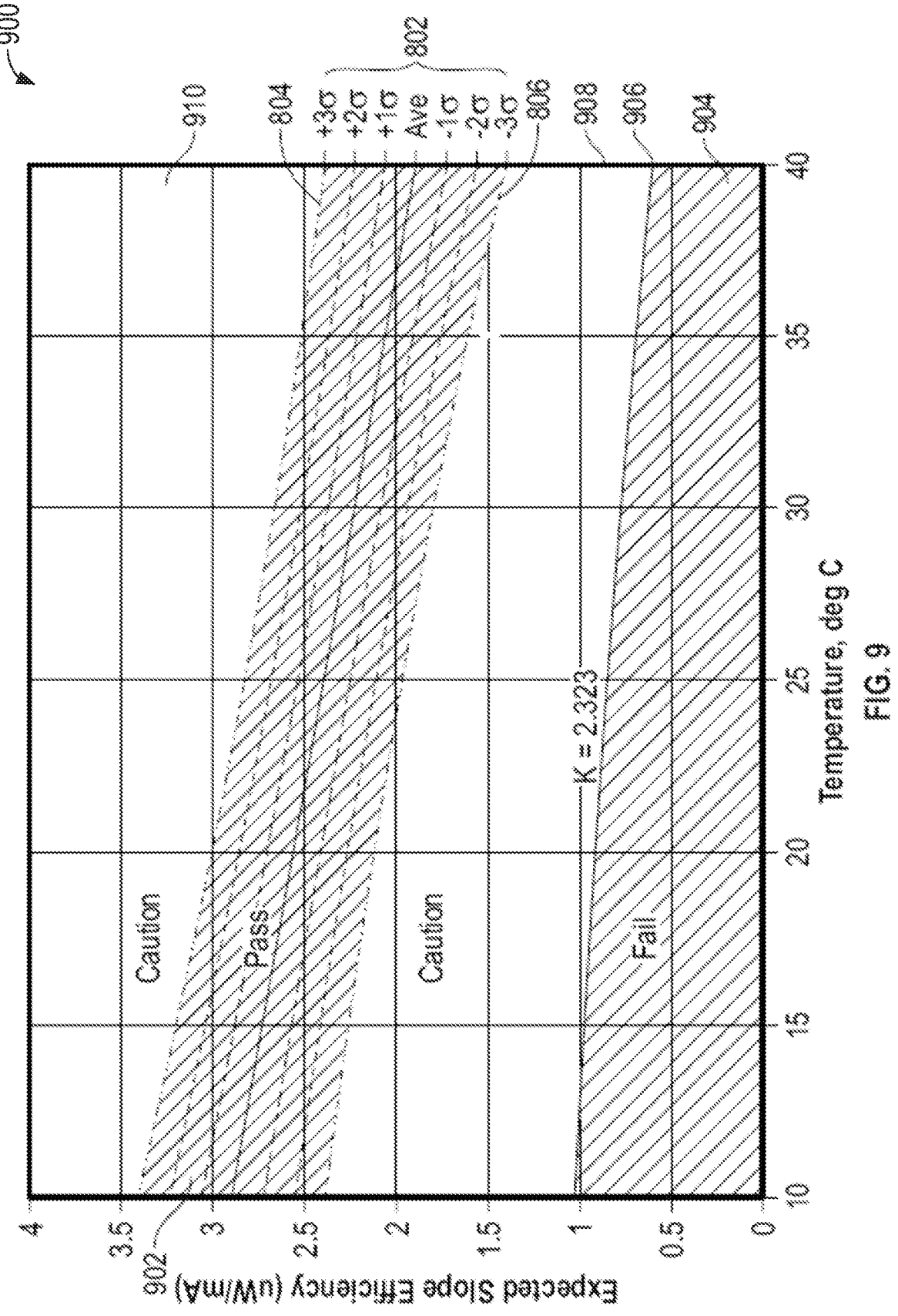
FIG. 9 graphically illustrates determining a result of a safety test of the red laser diode, according to certain embodiments.

In some cases, in order to determine the result of the safety test of the laser diode, the one or more processors 252 of the surgical laser system 202 may be further configured to determine whether the measured slope efficiency of the red laser diode 240 coincides with the range of the expected slope efficiency of the red laser diode 240. FIG. 9 graphically illustrates determining the result of the safety test based on whether the measured slope efficiency of the red laser diode 240 coincides with the range of the expected slope efficiency of the red laser diode 240.

For example, FIG. 9 illustrates a graph 900 including the area 802 representing a range of different expected slope efficiencies of the red laser diode 240 determined according to Equation 2 for different temperatures between $T_{min}$ and $T_{max}$. As noted above, the area 802 is bounded by a boundary line 804 representing the maximum expected slope efficiency for a particular temperature. As shown, the boundary line 804 represents three standard deviations ($+3\sigma$) above an expected slope efficiency for the particular temperature determined according to Equation 2. Similarly, as noted, the area 802 is bounded by a boundary line 806 representing the minimum expected slope efficiency for a particular temperature. As shown, the boundary line 806 represents three standard deviations ($+3\sigma$) below the expected slope efficiency for the particular temperature determined according to Equation 2.

As shown in FIG. 9, there are four different zones illustrated in the graph 900, each associated with a different safety test result outcome. For example, as shown, the graph 900 includes a first zone 902, coinciding with the area 802, that is associated with a passing safety test. When a measured slope efficiency (e.g., the measured slope efficiency determined at 440) of the red laser diode 240 coincides within the first zone 902, the result of the safety test may be considered a pass.

More specifically, for example, as noted above, determining the expected slope efficiency of the red laser diode 240 at 450 of FIG. 4 includes determining a range of the expected slope efficiency of the red laser diode 240 (e.g., for time t and the operating temperature measured at 410, T), comprising a number of standard deviations above and below the expected slope efficiency of the red laser diode 240, resulting in a maximum expected slope efficiency ($S_{max}$) and a minimum expected slope efficiency ($S_{min}$). Here, the maximum expected slope efficiency ($S_{max}$) and the minimum expected slope efficiency ($S_{min}$) are points on the boundary lines 804 and 806, respectively, for time t and temperature T (e.g., the operating temperature measured at 410) and define the first zone 902.

Accordingly, when the measured slope efficiency of the red laser diode 240 determined at 440 coincides with the range of the expected slope efficiency of the red laser diode 240 (e.g., measured slope efficiency coincides with the first zone 902 bounded between $S_{max}$ and $S_{min}$), the safety test of the red laser diode 240 may be considered a pass. In such cases, the electrical signal output by the one or more processors 252 may indicate on the display 256 that the red laser diode 240 passed the safety test. In general, a passing safety test may be defined according to Equation 3, below.

$$S_{expt} - 3\sigma_{S_{expt}} \leq S_{meas} \leq S_{expt} + 3\sigma_{S_{expt}} \tag{3}$$

In Equation 3, $S_{expt}$ is the expected slope efficiency of the red laser diode 240 determined at 450 of FIG. 4 for the measured operating temperature of the surgical laser system 202 determined at 410 of FIG. 4, $3\sigma_{S_{expt}}$ is the third standard deviation of the expected slope efficiency, and $S_{meas}$ is the measured slope efficiency of the red laser diode 240 determined at 440 of FIG. 4. Stated otherwise, $S_{expt} - 3\sigma_{S_{expt}}$ in Equation 3 is the minimum expected slope efficiency ($S_{min}$) for the measured operating temperature of the surgical laser system 202 while $S_{expt} + 3\sigma_{S_{expt}}$ in Equation 3 is the maximum expected slope efficiency ($S_{max}$) for the measured operating temperature of the surgical laser system 202.

Further, as shown, the graph 900 in FIG. 9 includes a second zone that is associated with a failing safety test. When a measured slope efficiency (e.g., the measured slope efficiency determined at 440) of the red laser diode 240 coincides within the second zone 904 bounded by a safety boundary line 906, the result of the safety test may be considered a fail.

As noted above, the red laser diode 240 is associated with a particular laser classification for performing ophthalmic surgery, such as laser classification type 2. In some cases, the safety threshold that defines the safety boundary line 906 may comprise a ratio (K) of a maximum output power associated with the particular laser classification of the red laser diode 240 ($P_2$) to a maximum output power associated with normal operation of the red laser diode 240 ($P_{max}$). In other words, the safety threshold may be defined according to $$K = P_2/P_{max}.$$

When the red laser diode is not operating normally, as is suggested when $S_{meas}$ is less than $S_{min}$, the estimated maximum power per laser spot $P_{max}'$ associated with the red laser diode 240 (e.g., depending on if the optical fiber 110 associated with the red laser diode 240 is single-core or multi-core) can be estimated as $$P_{max} \cdot (S_{min}/S_{meas}).$$

In some cases, K may be analogous to $$S_{min}/S_{meas}.$$

The maximum power per laser spot $P_{max}'$ is permitted to be as high as the Class 2 power per spot limit $P_2$, but no higher. Consequently, the low-power limit of $P_{meas}$ can be defined by Equation # and re-written equation #+1.

$$P_{max} \cdot (S_{min}/S_{meas}) \leq P_2 \qquad (4)$$

$$S_{meas} \geq S_{min}/K \qquad (5)$$

Since $S_{min}$ decreases with temperature T and K is a fixed constant, $S_{meas}$ decreases with temperature T as well. The safety boundary line 906 is the minimum permitted $S_{meas}$ versus temperature T threshold boundary at the edge of the second zone 904.

Accordingly, when the measured slope efficiency of the red laser diode 240 does not coincide with the range of the expected slope efficiency of the red laser diode 240 (e.g., the measured slope efficiency is not between $S_{max}$ and $S_{min}$) and when the measured slope efficiency of the laser diode is less than a safety threshold associated with the 240 laser diode (e.g., defining the safety boundary line 906 of the second zone 904), the result of the safety test may be considered a fail. In such cases, the electrical signal output by the one or more processors 252 at 470 of FIG. 4 may indicate that the red laser diode 240 failed the safety test. In some cases, the one or more processors 252 of the surgical laser system 202 may be configured to disable the red laser diode 240 in response to a failed safety test.

In general, a failing safety test may be defined according to Equation 6, below.

$$S_{meas} < (P_{max}/P_2) \cdot (S_{expt} - 3\sigma_{S_{expt}}) \qquad (6)$$

In Equation 6, $S_{meas}$ is the measured slope efficiency of the red laser diode 240 determined at 440 of FIG. 4, $P_{max}$ is the maximum output power associated with normal operation of the red laser diode 240, $P_2$ is the maximum output power associated with the particular laser classification of the red laser diode 240, $S_{expt}$ is the expected slope efficiency of the red laser diode 240 determined at 450 of FIG. 4 for the measured operating temperature of the surgical laser system 202 determined at 410 of FIG. 4, and $3\sigma_{S_{expt}}$ is the third standard deviation of the expected slope efficiency.

Accordingly, when the measured slope efficiency of the red laser diode 240 does not coincide with the range of the expected slope efficiency of the red laser diode 240 (e.g., the measured slope efficiency is not between $S_{max}$ and $S_{min}$) and when the measured slope efficiency of the laser diode is greater than or equal to the safety threshold associated with the red laser diode, the electrical signal output by the one or more processors 252 may indicate a cautionary condition associated with the safety test of the laser diode. For example, this cautionary condition may be indicated when the measured slope efficiency of the red laser diode 240 falls within either a third zone 908 or a fourth zone 910 of the graph 900 illustrated in FIG. 9.

If the measured slope efficiency of the red laser diode 240 falls within the third zone 908, the measured slope efficiency of the red laser diode 240 is lower than expected (e.g., lower than the minimum expected slope efficiency ($S_{min}$)). If this scenario is caused by a malfunction in a power monitoring circuit built into the red laser diode 240, there may be some instances in which the power monitoring circuit wrongly believes that not enough power is being supplied to the red laser diode 240 and responds by increasing the power supplied to the red laser diode 240, causing the red laser diode 240 to exceed the maximum output power associated with the particular laser classification of the red laser diode 240 ($P_2$). However, provided that the power supplied to the red laser diode 240 is not above $P_2$, then the red laser diode 240 may be permitted to continue to be used.

If the measured slope efficiency of the red laser diode 240 falls within the fourth zone 910, the measured slope efficiency of the red laser diode 240 is higher than expected (e.g., higher than the minimum expected slope efficiency ($S_{ma}$)). If this scenario is caused by a malfunction in the power monitoring circuit associated with the red laser diode 240, this malfunction may cause the red laser diode 240 to emit less laser light than expected. However, this may not cause eye safety issues, so use of the red laser diode 240 may still be permitted, although a cautionary condition may be indicated.

The techniques discussed above for performing a safety test of a red laser diode based on slope efficiency are advantageous for various reasons. For example, performing the safety test based on slope efficiency may not be vulnerable to diode-to-diode variation in performance characteristics since the slope efficiency check is based on performance characteristics of the red laser diode 240 characterized during calibration of the surgical laser system 202 (e.g., a step performed during the manufacturing process of the surgical laser system 202). Additionally, these techniques take into account and correct for the effects of the aging and temperature differences between calibration and future usage of the surgical laser system 202. For example, these techniques may not be vulnerable to small uncertainties in diode temperature since slope efficiency is only weakly dependent on temperature. Moreover, the safety test performed using the techniques presented herein is quick to perform and does not interfere with run time operation and provides a high level of confidence that usage of the red laser diode 240 during run time operation is safe.

FIG. 10 illustrates an exemplary diagram showing how various components of an ophthalmic surgery apparatus 1000 communicate and operate together. In some embodiments, the ophthalmic surgical apparatus 1000 may include the surgical laser system 202 described with respect to FIG. 2 that performs the process 400 for performing a safety test of a laser diode, such as the red laser diode 240.

As shown, the ophthalmic surgical apparatus 1000 includes, without limitation, a surgical laser system 1002, a display 1004, an interconnect 1006, and at least one I/O (Input/Output) device interface 1008, which may allow for the connection of various I/O devices (e.g., keyboards, displays, mouse devices, pen input, etc.) to the ophthalmic surgical apparatus 1000.

Further, as shown, the surgical laser system 1002, which may be an example of the surgical laser system 202 in FIG. 2, may include, without limitation, a temperature sensor 1010, a power module 1012, a red laser diode 1014, a central processing unit (CPU) 1016, and memory 1018. The surgical laser system 1002 may also include other components, such as those illustrated in and described with respect to FIG. 2.

In some cases, the temperature sensor 1010 may be configured to measure an operating temperature of the ophthalmic surgical apparatus 1000. Further, in some cases, power module 1012 may be configured to output a plurality of different current levels and apply the plurality of different current levels to an input of the red laser diode 1014. Further, in some cases, the power module 1012 may be configured to determine a plurality of different output power levels associated with the red laser diode 1014 based on the plurality of different current levels applied to the input of the red laser diode 1014. In some cases, the plurality of different output power levels includes a different output power for each of the different current levels of the plurality of different current levels.

In some cases, in order to determine the plurality of different output power levels associated with the laser diode, the power module 1012 may be further configured to measure a plurality of output voltage levels associated with the red laser diode 1014, each different output voltage level of the plurality of output voltage levels corresponding to a different current level of the plurality of different current levels applied to the input of the red laser diode 1014. The power module 1012 may then be configured to convert the plurality of output voltage levels to the plurality of different output power levels based on the plurality of different current levels applied to the input of the red laser diode 1014.

In some cases, the CPU 1016 may include one or more processors that may be configured to obtain the measured temperature of the ophthalmic surgical apparatus 1000 from the temperature sensor 1010. The CPU 1016 may also be configured to obtain, from the power module 1012, an indication of the plurality of different output power levels and the plurality of different current levels.

In some cases, the CPU 1016 may be further configured to determine a measured slope efficiency of the red laser diode 1014 based on the plurality of different current levels and the plurality of different output power levels. In some cases, in order to determine the measured slope efficiency of the laser diode, CPU 1016 may be further configured to determine a first difference between the plurality of different output power levels, determine a second difference between the plurality of different current levels, and determine a ratio of the first difference and the second difference. In such cases, the measured slope efficiency comprises the determined ratio.

In some cases, the CPU 1016 may be further configured to determine an expected slope efficiency of the red laser diode 1014 based on the measured operating temperature of the ophthalmic surgical apparatus. In some cases, the CPU 1016 may be further configured to determine the expected slope efficiency of the red laser diode 1014 based further on a calibration temperature associated with when the red laser diode 1014 was originally calibrated for the ophthalmic surgical apparatus 1000, a calibration slope efficiency associated with when the red laser diode 1014 was originally calibrated for the ophthalmic surgical apparatus 1000, and one or more aging correction factors. In some cases, indications of the calibration temperature, the calibration slope efficiency, and the one or more aging correction factors may be stored in the memory 1018.

In some cases, the CPU 1016 may be further configured to determine the expected slope efficiency of the laser diode according to: $S(t, T)=S_{cal} \cdot (1+C)+(1+R) \cdot S_o' \cdot (T-T_{cal})$, where $S(t, T)$ is the expected slope efficiency of the red laser diode 1014 at time t and measured operating temperature T, $S_{cal}$ is the calibration slope efficiency associated with the red laser diode 1014, C is a first aging correction factor for the calibration slope efficiency $S_{cal}$, $S_o'$ is a slope of the calibration slope efficiency, R is a second aging correction factor for the calibration slope efficiency $S_o'$, and $T_{cal}$ is the calibration temperature associated with the red laser diode 1014. In some cases, the slope of the calibration slope efficiency ($S_o'$) may also be stored in the memory 1018.

In some cases, the CPU 1016 may be further configured to determine a result of the safety test of the red laser diode 1014 based on the measured slope efficiency of the laser diode and an expected slope efficiency for the laser diode. In some cases, the CPU 1016 may be further configured to output an electrical signal indicating result of the safety test of the laser diode. In some cases, the display 1004 may be configured to receive the electrical signal from the CPU 1016 and to display the result of the safety test.

In some cases, the CPU 1016 may be further configured to determine a range of the expected slope efficiency of the red laser diode 1014, the range of the expected slope efficiency of the laser diode comprising a number of standard deviations above and below the expected slope efficiency of the red laser diode 1014. In some cases, the number of standard deviations comprises two or three standard deviations.

In some cases, in order to determine the result of the safety test of the red laser diode 1014, the CPU 1016 may be further configured to determine whether the measured slope efficiency of the red laser diode 1014 coincides with the range of the expected slope efficiency of the laser diode.

In some cases, when the measured slope efficiency of the red laser diode 1014 coincides with the range of the expected slope efficiency of the laser diode, the electrical signal output by the CPU 1016 indicates that the red laser diode 1014 passed the safety test.

In some cases, when the measured slope efficiency of the red laser diode 1014 does not coincide with the range of the expected slope efficiency of the red laser diode 1014 and when the measured slope efficiency of the red laser diode 1014 is less than a safety threshold associated with the red laser diode 1014, the electrical signal output by the CPU 1016 indicates that the red laser diode 1014 failed the safety test. In some cases, the red laser diode 1014 may be associated with a particular laser classification for performing ophthalmic surgery. In some cases, the safety threshold comprises a ratio of a maximum output power associated with the particular laser classification to a maximum output power associated with the red laser diode 1014. In some cases, the maximum output power associated with the particular laser classification and the maximum output power associated with the red laser diode 1014 may be stored in the memory 1018.

In some cases, when the measured slope efficiency of the red laser diode 1014 does not coincide with the range of the expected slope efficiency of the red laser diode 1014 and when the measured slope efficiency of the red laser diode 1014 is greater than or equal to the safety threshold associated with the red laser diode 1014, the electrical signal output by the CPU 1016 indicates a cautionary condition associated with the safety test of the red laser diode 1014.

In some cases, the CPU 1016 may retrieve and execute programming instructions stored in the memory 1018 for performing the process described with respect to FIG. 4, as well as other operations described herein for performing a safety test of a laser diode of an ophthalmic surgery apparatus. Similarly, CPU 1016 may retrieve and store application data residing in memory 1018. Interconnect 1006 transmits programming instructions and application data, among CPU 1016, at least one I/O device interface 1008, display 1004, memory 1018, power module 1012, temperature sensor 1010, red laser diode 1014, etc. The CPU 1016 can represent a single CPU, multiple CPUs, a single CPU having multiple processing cores, and the like. Additionally, in certain embodiments, memory 1018 may include volatile memory (e.g., random access memory). Furthermore, in certain embodiments, memory 1018 may also include non-volatile memory (e.g., a disk drive). Although shown as a single unit, memory 1018 may be a combination of fixed or removable storage devices, such as fixed disc drives, removable memory cards or optical storage, network attached storage (NAS), or a storage area-network (SAN).

Example Embodiments

Implementation examples are described in the following numbered clauses:

Embodiment 1: An apparatus for performing a safety test of a laser diode of an ophthalmic surgical apparatus, comprising: a temperature sensor configured to measure an operating temperature of the ophthalmic surgical apparatus; a power module configured to: output a plurality of different current levels; apply the plurality of different current levels to an input of the laser diode; and determine a plurality of different output power levels associated with the laser diode based on the plurality of different current levels applied to the input of the laser diode, wherein the plurality of different output power levels include a different output power for each of the different current levels of the plurality of different current levels; one or more processors configured to: obtain the measured operating temperature of the ophthalmic surgical apparatus from the temperature sensor; obtain, from the power module, an indication of the plurality of different output power levels and the plurality of different current levels; determine a measured slope efficiency of the laser diode based on the plurality of different current levels and the plurality of different output power levels; determine an expected slope efficiency of the laser diode based on the measured operating temperature of the ophthalmic surgical apparatus; determine a result of the safety test of the laser diode based on the measured slope efficiency of the laser diode and the expected slope efficiency for the laser diode; and output an electrical signal indicating result of the safety test of the laser diode.

Embodiment 2: The apparatus of Embodiment 1, wherein, in order to determine the plurality of different output power levels associated with the laser diode, the power module is further configured to: measure a plurality of output voltage levels associated with the laser diode, each different output voltage level of the plurality of output voltage levels corresponding to a different current level of the plurality of different current levels applied to the input of the laser diode, and convert the plurality of output voltage levels to the plurality of different output power levels based on the plurality of different current levels applied to the input of the laser diode.

Embodiment 3: The apparatus of any one of Embodiments 1-2, wherein, in order to determine the measured slope efficiency of the laser diode, the one or more processors are further configured to: determine a first difference between the plurality of different output power levels, determine a second difference between the plurality of different current levels, and determine a ratio of the first difference and the second difference, wherein the measured slope efficiency comprises the determined ratio.

Embodiment 4: The apparatus of any one of Embodiments 1-3, wherein the one or more processors are further configured to determine the expected slope efficiency of the laser diode based further on a calibration temperature associated with when the laser diode was originally calibrated for the ophthalmic surgical apparatus, a calibration slope efficiency associated with when the laser diode was originally calibrated for the ophthalmic surgical apparatus, and one or more aging correction factors.

Embodiment 5: The apparatus of Embodiment 4, wherein the one or more processors are further configured to determine the expected slope efficiency of the laser diode according to: $S(t, T)=S_{cal}\cdot(1+C)+(1+R)\cdot S_o'\cdot(T-T_{cal})$, where $S(t, T)$ is the expected slope efficiency of the laser diode at time t and measured operating temperature T, $S_{cal}$ is the calibration slope efficiency associated with the laser diode, C is a first aging correction factor for the calibration slope efficiency $S_{cal}$, $S_o'$ is a slope of the calibration slope efficiency, R is a second aging correction factor for the calibration slope efficiency $S_o'$, and $T_{cal}$ is the calibration temperature associated with the laser diode Embodiment 6: The apparatus of any one of Embodiments 1-5, wherein the one or more processors are further configured to determine a range of the expected slope efficiency of the laser diode, the range of the expected slope efficiency of the laser diode comprising a number of standard deviations above and below the expected slope efficiency of the laser diode.

Embodiment 7: The apparatus of Embodiment 6, wherein the number of standard deviations comprises two or three standard deviations.

Embodiment 8: The apparatus of any one of Embodiments 6-7, wherein, in order to determine the result of the safety test of the laser diode, the one or more processors are further configured to determine whether the measured slope efficiency of the laser diode coincides with the range of the expected slope efficiency of the laser diode.

Embodiment 9: The apparatus of Embodiment 8, wherein, when the measured slope efficiency of the laser diode coincides with the range of the expected slope efficiency of the laser diode, the electrical signal output by the one or more processors indicates that the laser diode passed the safety test.

Embodiment 10: The apparatus of any one of Embodiments 8-9, wherein, when the measured slope efficiency of the laser diode does not coincide with the range of the expected slope efficiency of the laser diode and when the measured slope efficiency of the laser diode is less than a safety threshold associated with the laser diode, the electrical signal output by the one or more processors indicates that the laser diode failed the safety test.

Embodiment 11: The apparatus of Embodiment 10, wherein, when the measured slope efficiency of the laser diode does not coincide with the range of the expected slope efficiency of the laser diode and when the measured slope efficiency of the laser diode is greater than or equal to the safety threshold associated with the laser diode, the electrical signal output by the one or more processors indicates a cautionary condition associated with the safety test of the laser diode.

Embodiment 12: The apparatus of any one of Embodiments 10-11, wherein: the laser diode is associated with a particular laser classification for performing ophthalmic surgery, and the safety threshold comprises a ratio of a maximum output power associated with the particular laser classification to a maximum output power associated with the laser diode.

Embodiment 13: The apparatus of any one of Embodiments 10-12, wherein the one or more processors are further configured to disable the laser diode in response to the failed safety test.

Embodiment 14: A method for performing a safety test of a laser diode associated with an ophthalmic surgical apparatus, comprising: measuring an operating temperature of the ophthalmic surgical apparatus; outputting a plurality of different current levels and applying the plurality of different current levels to an input of the laser diode; determining a plurality of different output power levels associated with the laser diode based on the plurality of different current levels applied to the input of the laser diode, wherein the plurality of different output power levels include a different output power for each of the different current levels of the plurality of different current levels; determining a measured slope efficiency of the laser diode based on the plurality of different current levels and the plurality of different output power levels; determining an expected slope efficiency of the laser diode based on the measured operating temperature of the ophthalmic surgical apparatus; determining a result of the safety test of the laser diode based on the measured slope efficiency of the laser diode and the expected slope efficiency for the laser diode; and outputting an electrical signal indicating result of the safety test of the laser diode.

Embodiment 15: The method of Embodiment 14, wherein determining the plurality of different output power levels associated with the laser diode comprises: measuring a plurality of output voltage levels associated with the laser diode, each different output voltage level of the plurality of output voltage levels corresponding to a different current level of the plurality of different current levels applied to the input of the laser diode, and converting the plurality of output voltage levels to the plurality of different output power levels based on the plurality of different current levels applied to the input of the laser diode.

Embodiment 16: The method of any one of Embodiments 14-15, wherein determining the measured slope efficiency of the laser diode comprises: determining a first difference between the plurality of different output power levels, determining a second difference between the plurality of different current levels, and determining a ratio of the first difference and the second difference, wherein the measured slope efficiency comprises the determined ratio.

Embodiment 17: The method of any one of Embodiments 14-16, wherein determining the expected slope efficiency of the laser diode is based further on a calibration temperature associated with when the laser diode was originally calibrated for the ophthalmic surgical apparatus, a calibration slope efficiency associated with when the laser diode was originally calibrated for the ophthalmic surgical apparatus, and one or more aging correction factors.

Embodiment 18: The method of Embodiment 17, wherein determining the expected slope efficiency of the laser diode comprises determining the expected slope efficiency of the laser diode according to: $S(t, T)=S_{cal} \cdot (1+C)+(1+R) \cdot S_o' \cdot (T-T_{cal})$, where $S(t, T)$ is the expected slope efficiency of the laser diode at time t and measured operating temperature T, $S_{cal}$ is the calibration slope efficiency associated with the laser diode, C is a first aging correction factor for the calibration slope efficiency $S_{cal}$, $S_o'$ is a slope of the calibration slope efficiency, R is a second aging correction factor for the calibration slope efficiency $S_o'$, and $T_{cal}$ is the calibration temperature associated with the laser diode.

Embodiment 19: The method of any one of Embodiments 14-18, further comprising determining a range of the expected slope efficiency of the laser diode, the range of the expected slope efficiency of the laser diode comprising a number of standard deviations above and below the expected slope efficiency of the laser diode.

Embodiment 20: The method of Embodiment 19, wherein the number of standard deviations comprises two or three standard deviations.

Embodiment 21: The method of any one of Embodiments 19-20, wherein determining the result of the safety test of the laser diode comprises determining whether the measured slope efficiency of the laser diode coincides with the range of the expected slope efficiency of the laser diode.

Embodiment 22: The method of Embodiment 21, wherein, when the measured slope efficiency of the laser diode coincides with the range of the expected slope efficiency of the laser diode, the outputted electrical signal indicates that the laser diode passed the safety test.

Embodiment 23: The method of any one of Embodiments 21-22, wherein, when the measured slope efficiency of the laser diode does not coincide with the range of the expected slope efficiency of the laser diode and when the measured slope efficiency of the laser diode is less than a safety threshold associated with the laser diode, the outputted electrical signal indicates that the laser diode failed the safety test.

Embodiment 24: The method of Embodiment 23, wherein, when the measured slope efficiency of the laser diode does not coincide with the range of the expected slope efficiency of the laser diode and when the measured slope efficiency of the laser diode is greater than or equal to the safety threshold associated with the laser diode, the outputted electrical signal indicates a cautionary condition associated with the safety test of the laser diode.

Embodiment 25: The method of any one of Embodiments 23-24, wherein: the laser diode is associated with a particular laser classification for performing ophthalmic surgery, and the safety threshold comprises a ratio of a maximum output power associated with the particular laser classification to a maximum output power associated with the laser diode Embodiment 26: The method of any one of Embodiments 23-25, further comprising disabling the laser diode in response to the failed safety test.

Embodiment 27: An apparatus, comprising means for performing a method in accordance with any of Embodiments 14-26.

Embodiment 28: A non-transitory computer-readable medium comprising executable instructions that, when executed by a processor of an apparatus, cause the apparatus to perform a method in accordance with any of Embodiments 14-26.

Embodiment 29: A computer program product embodied on a computer-readable storage medium comprising code for performing a method in accordance with any of Embodiments 14-26.

ADDITIONAL CONSIDERATIONS

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

The foregoing description is provided to enable any person skilled in the art to practice the various embodiments described herein. Various modifications to these embodiments will be readily apparent to those skilled in the art, and the generic principles defined herein may be applied to other embodiments. Thus, the claims are not intended to be limited to the embodiments shown herein, but are to be accorded the full scope consistent with the language of the claims.

Within a claim, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112(f) unless the element is expressly recited using the phrase "means for" or, in the case of a method claim, the element is recited using the phrase "step for." The word "exemplary" is used herein to mean "serving as an example, instance, or illustration." Any aspect described herein as "exemplary" is not necessarily to be construed as preferred or advantageous over other aspects.

What is claimed is:

1. An apparatus for performing a safety test of a laser diode of an ophthalmic surgical apparatus, comprising:
   a temperature sensor configured to measure an operating temperature of the ophthalmic surgical apparatus;
   a power module comprising circuitry, the power module configured to:
   output a plurality of different current levels;

24 apply the plurality of different current levels to an input of the laser diode; and
determine a plurality of different output power levels associated with the laser diode based on the plurality of different current levels applied to the input of the laser diode, wherein the plurality of different output power levels include a different output power for each of the different current levels of the plurality of different current levels;
one or more processors configured to:
   obtain the measured operating temperature of the ophthalmic surgical apparatus from the temperature sensor;
   obtain, from the power module, an indication of the plurality of different output power levels and the plurality of different current levels;
   determine a measured slope efficiency of the laser diode based on the plurality of different current levels and the plurality of different output power levels;
   determine an expected slope efficiency of the laser diode based on the measured operating temperature of the ophthalmic surgical apparatus and one or more calibration parameters;
   determine a result of the safety test of the laser diode based on the measured slope efficiency of the laser diode and the expected slope efficiency for the laser diode; and
   output an electrical signal indicating result of the safety test of the laser diode.

2. The apparatus of claim 1, wherein, in order to determine the plurality of different output power levels associated with the laser diode, the power module is further configured to:
   measure a plurality of output voltage levels associated with the laser diode, each different output voltage level of the plurality of output voltage levels corresponding to a different current level of the plurality of different current levels applied to the input of the laser diode, and
   convert the plurality of output voltage levels to the plurality of different output power levels based on the plurality of different current levels applied to the input of the laser diode.

3. The apparatus of claim 1, wherein, in order to determine the measured slope efficiency of the laser diode, the one or more processors are further configured to:
   determine a first difference between the plurality of different output power levels,
   determine a second difference between the plurality of different current levels, and
   determine a ratio of the first difference and the second difference, wherein the measured slope efficiency comprises the determined ratio.

4. The apparatus of claim 1, wherein the one or more calibration parameters comprise a calibration temperature associated with when the laser diode was originally calibrated for the ophthalmic surgical apparatus and a calibration slope efficiency associated with when the laser diode was originally calibrated for the ophthalmic surgical apparatus, and wherein the one or more processors are further configured to determine the expected slope efficiency of the laser diode based further on one or more aging correction factors.

5. The apparatus of claim 4, wherein the one or more processors are further configured to determine the expected slope efficiency of the laser diode according to:

25 26

$$S(t, T) = S_{cal} \cdot (1 + C) + (1 + R) \cdot S'_o \cdot (T - T_{cal}),$$

where S(t, T) is the expected slope efficiency of the laser diode at time t and measured operating temperature T, $S_{cal}$ is the calibration slope efficiency associated with the laser diode, C is a first aging correction factor for the calibration slope efficiency $S_{cal}$, $S'_o$ is a slope of the calibration slope efficiency, R is a second aging correction factor for the calibration slope efficiency $S'_o$, and $T_{cal}$ is the calibration temperature associated with the laser diode.

6. The apparatus of claim 1, wherein the one or more processors are further configured to determine a range of the expected slope efficiency of the laser diode, the range of the expected slope efficiency of the laser diode comprising a number of standard deviations above and below the expected slope efficiency of the laser diode.

7. The apparatus of claim 6, wherein the number of standard deviations comprises two or three standard deviations.

8. The apparatus of claim 6, wherein, in order to determine the result of the safety test of the laser diode, the one or more processors are further configured to determine whether the measured slope efficiency of the laser diode coincides with the range of the expected slope efficiency of the laser diode.

9. The apparatus of claim 8, wherein, when the measured slope efficiency of the laser diode coincides with the range of the expected slope efficiency of the laser diode, the electrical signal output by the one or more processors indicates that the laser diode passed the safety test.

10. The apparatus of claim 8, wherein, when the measured slope efficiency of the laser diode does not coincide with the range of the expected slope efficiency of the laser diode and when the measured slope efficiency of the laser diode is less than a safety threshold associated with the laser diode, the electrical signal output by the one or more processors indicates that the laser diode failed the safety test.

11. The apparatus of claim 10, wherein, when the measured slope efficiency of the laser diode does not coincide with the range of the expected slope efficiency of the laser diode and when the measured slope efficiency of the laser diode is greater than or equal to the safety threshold associated with the laser diode, the electrical signal output by the one or more processors indicates a cautionary condition associated with the safety test of the laser diode.

12. The apparatus of claim 10, wherein:
the laser diode is associated with a particular laser classification for performing ophthalmic surgery, and the safety threshold comprises a ratio of a maximum output power associated with the particular laser classification to a maximum output power associated with the laser diode.

13. The apparatus of claim 10, wherein the one or more processors are further configured to disable the laser diode in response to the failed safety test.

14. A method for performing a safety test of a laser diode associated with an ophthalmic surgical apparatus, comprising:
measuring an operating temperature of the ophthalmic surgical apparatus;
outputting a plurality of different current levels and applying the plurality of different current levels to an input of the laser diode;
determining a plurality of different output power levels associated with the laser diode based on the plurality of different current levels applied to the input of the laser diode, wherein the plurality of different output power levels include a different output power for each of the different current levels of the plurality of different current levels;
determining a measured slope efficiency of the laser diode based on the plurality of different current levels and the plurality of different output power levels;
determining an expected slope efficiency of the laser diode based on the measured operating temperature of the ophthalmic surgical apparatus and one or more calibration parameters;
determining a result of the safety test of the laser diode based on the measured slope efficiency of the laser diode and the expected slope efficiency for the laser diode; and
outputting an electrical signal indicating result of the safety test of the laser diode.

15. The method of claim 14, wherein determining the plurality of different output power levels associated with the laser diode comprises:
measuring a plurality of output voltage levels associated with the laser diode, each different output voltage level of the plurality of output voltage levels corresponding to a different current level of the plurality of different current levels applied to the input of the laser diode, and
converting the plurality of output voltage levels to the plurality of different output power levels based on the plurality of different current levels applied to the input of the laser diode.

* * * * *